US009301917B2

(12) United States Patent
Fukushima et al.

(10) Patent No.: US 9,301,917 B2
(45) Date of Patent: Apr. 5, 2016

(54) SUSTAINED-RELEASE PHARMACEUTICAL COMPOSITION

(75) Inventors: Masanori Fukushima, Kyoto (JP); Hiroaki Matsubara, Kyoto (JP); Satoaki Matoba, Kyoto (JP); Shigeki Hijikata, Tokyo (JP); Yu Aso, Tokyo (JP); Tsutomu Sato, Tokyo (JP)

(73) Assignees: Kyoto University, Kyoto (JP); Kyoto Prefectural Public University Corporation, Kyoto (JP); Kaken Pharmaceutical Co., Ltd., Tokyo (JP); Koken Co., Ltd., Tokyo (JP)

( * ) Notice: Subject to any disclaimer, the term of this patent is extended or adjusted under 35 U.S.C. 154(b) by 0 days.

(21) Appl. No.: 13/824,598

(22) PCT Filed: Oct. 14, 2011

(86) PCT No.: PCT/JP2011/073632
§ 371 (c)(1),
(2), (4) Date: May 15, 2013

(87) PCT Pub. No.: WO2012/050184
PCT Pub. Date: Apr. 19, 2012

(65) Prior Publication Data
US 2013/0225492 A1    Aug. 29, 2013

(30) Foreign Application Priority Data

Oct. 15, 2010   (JP) ................................. 2010-232113

(51) Int. Cl.
| | |
|---|---|
| *A61K 38/00* | (2006.01) |
| *A61K 9/00* | (2006.01) |
| *A61K 31/7004* | (2006.01) |
| *A61K 31/7008* | (2006.01) |
| *A61K 45/06* | (2006.01) |
| *A61K 38/39* | (2006.01) |
| *A61K 9/51* | (2006.01) |
| *A61K 47/26* | (2006.01) |
| *A61K 47/42* | (2006.01) |
| *A61K 38/27* | (2006.01) |
| *A61K 38/18* | (2006.01) |

(52) U.S. Cl.
CPC ............ *A61K 9/0002* (2013.01); *A61K 9/0024* (2013.01); *A61K 9/5123* (2013.01); *A61K 31/7004* (2013.01); *A61K 31/7008* (2013.01); *A61K 38/1825* (2013.01); *A61K 38/39* (2013.01); *A61K 45/06* (2013.01); *A61K 47/26* (2013.01); *A61K 47/42* (2013.01); *A61K 38/1808* (2013.01); *A61K 38/1816* (2013.01); *A61K 38/1858* (2013.01); *A61K 38/27* (2013.01)

(58) Field of Classification Search
CPC .................... A61K 9/0002; A61K 38/1825
See application file for complete search history.

(56) References Cited

U.S. PATENT DOCUMENTS

| | | | |
|---|---|---|---|
| 7,052,875 B1 * | 5/2006 | Terada et al. ............... | 435/91.1 |
| 2004/0047892 A1 | 3/2004 | Desrosiers et al. | |
| 2011/0028699 A1 * | 2/2011 | Ono ............................ | 530/399 |

FOREIGN PATENT DOCUMENTS

| | | | |
|---|---|---|---|
| JP | 56122317 A | | 9/1981 |
| JP | 62-228028 A | | 10/1987 |
| JP | 05043453 A | | 2/1993 |
| JP | 10167987 A | | 6/1998 |
| WO | WO 93/21908 | * | 11/1993 |
| WO | 0240072 A2 | | 5/2002 |
| WO | WO 02/40072 | * | 5/2002 |
| WO | 2008120741 A1 | | 10/2008 |

OTHER PUBLICATIONS

Ribatti et al, Endogenous and exogenous fibrobroblast growth factor-2 modulate wound healing in the chick embryo chorioallantoic membrane, Angiogenesis 3: 89-95, 1999.*
Seghezzi et al, Fibroblast Growth Factor-2 (FGF-2) Induces Vascular Endothelial Growth Factor (VEGF) Expression in the Endothelial Cells of Forming Capillaries: An Autocrine Mechanism Contributing to Angiogenesis, The Journal of Cell Biology, vol. 141, No. 7, Jun. 29, 1998 1659-1673).*
International Search Report issued in corresponding International Patent Application No. PCT/JP2011/073632 dated Dec. 27, 2011 (3 pages).
Hayashi et al., "Factors Affecting the Interactions of Collagen Molecules as Observed by in Vitro Fibril Formation", J. Biochem., vol. 72, No. 3, (1972), p. 749-758.
Kuznetsova et al., "Sugars and Polyols Inhibit Fibrillogenesis of Type I Collagen by Disrupting Hydrogen-Bonded Water Bridges between the Helices", Biochemistry, vol. 37, (1998), pp. 11888-11895.
Office Action issued in corresponding Japanese Patent Application No. 2012-538723 dated Aug. 10, 2015 (9 pages).
Wallace et al., "Collagen gel systems for sustained delivery and tissue engineering", Advanced Drug Delivery Reviews, vol. 55, (2003), pp. 1631-1649.
Wallace et al., "Shear creep of injectable collagen biomaterials", Journal of Biomedical Materials Research, vol. 21, (1987), pp. 861-880.

* cited by examiner

Primary Examiner — Karlheinz R Skowronek
Assistant Examiner — Sergio Coffa
(74) Attorney, Agent, or Firm — Kilyk & Bowersox, P.L.L.C.

(57) ABSTRACT

Provided is a pharmaceutical composition, including a drug and a collagen, in which the composition is satisfactory in handleability and has sustained-release property. The sustained-release pharmaceutical composition includes: a drug; a collagen; and at least one kind of sugar selected from monosaccharides, disaccharides, trisaccharides, and tetrasaccharides. The inventors of the present invention have found that the in vivo administration of a collagen solution containing a sugar results in the gelation of a collagen. Based on this finding, the inventors have found that a composition containing a drug, a collagen, and a sugar can control the release rate of the drug, and such composition can be used as a sustained-release pharmaceutical composition.

11 Claims, 13 Drawing Sheets

SUSTAINED-RELEASE PHARMACEUTICAL COMPOSITION

The present application is a National Stage Application of PCT/JP2011/073632, filed Oct. 14, 2011, which claims priority from Japanese Patent Application No. 2010-232113, which is hereby incorporated by reference.

TECHNICAL FIELD

The present invention relates to a sustained-release pharmaceutical composition and a method of manufacturing a sustained-release pharmaceutical composition.

The present application claims priority from Japanese Patent Application No. 2010-232113, which is hereby incorporated by reference.

BACKGROUND ART

Hitherto, a polymer material has been widely utilized in a sustained-release pharmaceutical composition because it allows a concentration of a drug in a tissue to be effectively retained over a long period. The polymer material has such characteristics that the material can bind a drug in a physical or chemical manner and releases the drug along with progression of its in vivo degradation. Such polymer material is exemplified by a cellulose derivative, a starch derivative, a dextran derivative, a polysaccharide, a protein, a polypeptide, an acrylic acid derivative, or a vinyl derivative.

As a sustained-release characteristic of a drug mediated by a collagen as the protein, it is known that a sustained-release period of a drug can be controlled to a short period (about several days) to a long period (several months) by regulating a collagen concentration. For example, Patent Literature 1 discloses that when the collagen concentration is reduced, degradation of a gelated collagen containing a drug is accelerated, sustained release of the drug is also accelerated, and thus a drug efficacy period is completed within a short period, and in contrast, that when the collagen concentration is increased, degradation of a gelated collagen is delayed, sustained release of the drug is also delayed, and thus drug efficacy can be exhibited for a long period. However, when the collagen concentration is high, a sophisticated technology is required because of difficulty in formulation. Further, in contrast, when the collagen concentration is low, although operations such as injection into a tissue and addition and mixing of a drug become easy, there is a problem, for example, in that a drug sustained-release rate after injection into a tissue becomes high, drug efficacy is exhibited within only a short period, and sustained-release for a long period is not attained, with the result that drug efficacy is not sufficiently obtained.

Patent Literature 2 discloses a local sustained-release formulation for wound healing promotion obtained by mixing a carrier containing a collagen as an essential constituent with a physiologically active substance having a wound healing promoting activity. The carrier described in Patent Literature 2 is constructed of ingredients selected from the group consisting of proteins such as a collagen and an albumin, carbohydrates such as a chitin, and synthetic polymers. Patent Literature 2 discloses that a sustained-release characteristic of a drug depends on dosage forms such as a powder and a film. However, it takes much time to form the formulation into any of those dosage forms, and thus the formulation is lack of convenience. Further, Patent Literature 3 discloses a sustained-release formulation containing a collagen, a glycosaminoglycan as a polysaccharide, and a drug. Patent Literature 3 discloses that the glycosaminoglycan controls fibrillogenesis of the collagen and functions as a release control factor for the drug. The sustained-release formulation of Patent Literature 3 is a solid formulation, is formed into a dosage form such as a needle or a stick, and hence is lack of convenience as with the formulation described in Patent Literature 2.

It is known that a collagen solution undergoes gelation when heated to around a body temperature in vitro, and it is also known that addition of a sugar such as a monosaccharide or a disaccharide to a collagen solution in advance inhibits gelation of the solution (Non Patent Literature 1 and Non Patent Literature 2). In a state in which the gelation is inhibited, it is considered that a sustained-release characteristic of a drug mediated by a collagen is not sufficiently exhibited. Hence, in applying the collagen as a carrier for a sustained-release pharmaceutical, it has been impossible to employ a technology for inhibiting gelation using the collagen in combination with a sugar such as a monosaccharide.

CITATION LIST

Patent Literature

[PTL 1] JP 56-122317 A
[PTL 2] JP 05-043453 A
[PTL 3] JP 10-167987 A

Non Patent Literature

[NPL1] Hayashi et al., Factors Affecting the Interaction of Collagen Molecules as Observed by in Vitro Fibril Formation, J. Biochem., (1972) 72, 749

[NPL2] Kuznetsova et al., Sugars and Polyols Inhibit Fibrillogenesis of Type I Collagen by Disrupting Hydrogen-Bonded Water Bridges between the Helices, Biochemistry, (1998) 37, 11888

SUMMARY OF INVENTION

Technical Problem

An object of the present invention is to provide a pharmaceutical composition, including a drug and a collagen, in which the composition is satisfactory in handleability and has sustained-release property.

Solution to Problem

It is known that the addition of a sugar to a collagen solution inhibits the gelation of the solution. In contrast, the inventors of the present invention have surprisingly found that the in vivo administration of a collagen solution containing a sugar results in the gelation of a collagen. Based on this finding, the inventors have focused attention on the fact that a composition containing a drug, a collagen, and a sugar can control the release rate of the drug, and such composition can be used as a sustained-release pharmaceutical composition. Thus, the present invention has been accomplished.

That is, the present invention includes the following items.
1. A sustained-release pharmaceutical composition, including: a drug; a collagen; and at least one kind of sugar selected from monosaccharides, disaccharides, trisaccharides, and tetrasaccharides.
2. A sustained-release pharmaceutical composition according to the above-mentioned item 1, in which the sugar has such a concentration in the composition before administration to a body that the sugar inhibits gelation of the collagen.

3. A sustained-release pharmaceutical composition according to the above-mentioned item 1 or 2, in which the sugar includes at least one kind of sugar selected from disaccharides and trisaccharides.

4. A sustained-release pharmaceutical composition according to the above-mentioned items 1 to 3, in which a concentration of the collagen is 0.01 to 30% by weight, and a concentration of the sugar is 0.01 M to 3 M.

5. A sustained-release pharmaceutical composition according to any one of the above-mentioned items 1 to 4, in which the collagen includes a collagen having a molecular weight of 1 kDa to 2,000 kDa.

6. A sustained-release pharmaceutical composition according to any one of the above-mentioned items 1 to 5, in which the collagen includes atelocollagen.

7. A sustained-release pharmaceutical composition according to any one of the above-mentioned items 1 to 6, in which the sustained-release pharmaceutical composition is in a liquid form before administration to a body, and has property of undergoing gelation after the administration.

8. A sustained-release pharmaceutical composition according to any one of the above-mentioned items 1 to 7, in which the sustained-release pharmaceutical composition controls a release rate of the drug.

9. A sustained-release pharmaceutical composition according to any one of the above-mentioned items 1 to 8, in which the drug includes a protein.

10. A sustained-release pharmaceutical composition according to any one of the above-mentioned items 1 to 9, in which the sustained-release pharmaceutical composition includes an angiogenesis regulator.

11. A sustained-release pharmaceutical composition according to any one of the above-mentioned items 1 to 10, in which the drug includes bFGF.

12. A sustained-release pharmaceutical composition according to any one of the above-mentioned items 1 to 11, in which the sustained-release pharmaceutical composition is in a form of a liquid formulation.

13. A sustained-release pharmaceutical composition according to any one of the above-mentioned items 1 to 12, in which the sustained-release pharmaceutical composition is administered by an administration route selected from the group consisting of intradermal administration, subcutaneous administration, intramuscular administration, intracavity administration, direct administration to an organ, and direct administration to a tissue.

14. A sustained-release pharmaceutical composition according to any one of the above-mentioned items 1 to 13, in which the sustained-release pharmaceutical composition is used for treatment of a vascular occlusive disease and/or an ischemic disease.

15. A method of manufacturing a sustained-release pharmaceutical composition, the method including mixing: a drug; a collagen; and at least one kind of sugar selected from monosaccharides, disaccharides, trisaccharides, and tetrasaccharides.

16. A method of manufacturing a sustained-release pharmaceutical composition according to the above-mentioned item 15, in which the sugar has such a concentration that the sugar inhibits gelation of the collagen.

17. A sustained-release base, including: a collagen; and at least one kind of sugar selected from monosaccharides, disaccharides, trisaccharides, and tetrasaccharides.

18. A sustained-release base according to the above-mentioned item 17, in which the sustained-release base is in a liquid form.

19. A sustained-release base according to the above-mentioned item 17 or 18, in which the sustained-release base is used for manufacture of a sustained-release pharmaceutical composition.

20. A method of controlling a drug release rate from a sustained-release pharmaceutical composition, the method including blending a collagen with at least one kind of sugar selected from monosaccharides, disaccharides, trisaccharides, and tetrasaccharides in a sustained-release pharmaceutical composition.

Advantageous Effects of Invention

According to the sustained-release pharmaceutical composition of the present invention, it is possible to achieve the controlled release of the drug as an active ingredient in an embodiment mode using immediately effective release and slow sustained release in combination in vivo. According to the sustained-release pharmaceutical composition of the present invention, immediately effective drug release can be attained by virtue of the fact that the addition of the sugar inhibits the gelation of the collagen in the initial period after the administration, and slow sustained-release can be attained by virtue of the fact that the in vivo gelation of the collagen occurs in a time-dependent manner after the administration, resulting in a reduction in release rate of the drug.

Further, in general, in the preparation of a pharmaceutical composition having added thereto a collagen, it is necessary to manage a temperature so as to prevent the gelation of the collagen. In the sustained-release pharmaceutical composition of the present invention, the addition of the sugar to the collagen inhibits such gelation, which can facilitate a preparation operation at room temperature.

BRIEF DESCRIPTION OF DRAWINGS

FIGS. 3a to 3c show the results of the respective formulations described in Example 2, and FIG. 3d shows the result of a formulation as a control. P means lysozyme, S means sucrose, and AC means atelocollagen (Example 2).

FIG. 5a shows the result in the case where the drug is transferrin, FIG. 5b shows the result in the case where the drug is phosphorylase b, FIG. 5c shows the result in the case where the drug is myosin heavy chain, FIG. 5d shows the result in the case where the drug is ferritin type I, and FIG. 5e shows the result in the case where the drug is thyrogloblin (Example 4).

FIG. 6a shows the result of a formulation containing 2 mg/mL bFGF, 0.25 M sucrose, and a collagen at 3% [w/v], FIG. 6b shows the result of a formulation containing 2 mg/mL bFGF and a collagen at 3% [w/v] and containing no sucrose, and FIG. 6c shows the result of a formulation containing no bFGF and no sucrose and containing a collagen only at 3% [w/v] (Example 5).

FIGS. 16a to 16j show the results of formulations containing sugars shown in Table 3 (Example 9).

DESCRIPTION OF EMBODIMENTS

Figure 1:
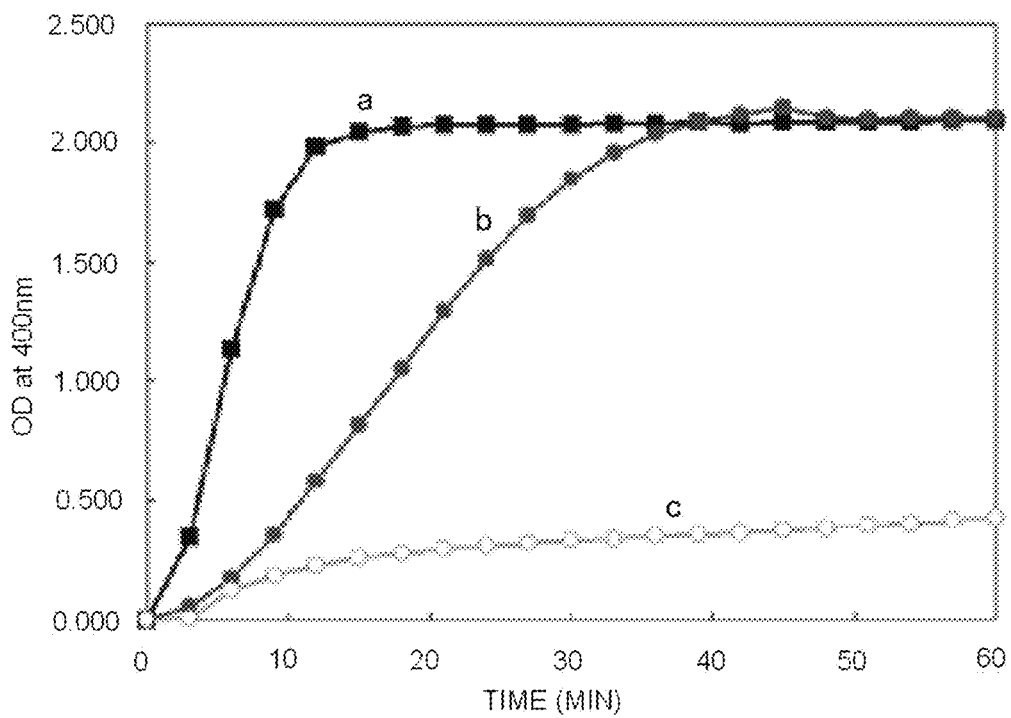
[FIG. 1] A graph showing a collagen gelation inhibiting action of sugar addition. In the figure, "a" shows the result in the case of a collagen only, "b" shows the result in the case of blending a collagen and 0.01 M sucrose, and "c" shows the result in the case of blending a collagen and 0.25 M sucrose (Reference Example 1).

The present invention relates to a sustained-release pharmaceutical composition, including: a drug; a collagen; and at least one kind of sugar selected from monosaccharides, disaccharides, trisaccharides, and tetrasaccharides.

By virtue of containing the at least one kind of sugar, the sustained-release pharmaceutical composition of the present invention is in a liquid form before in vivo administration, and underdoes gelation after in vivo administration. The gelation of the sustained-release pharmaceutical composition of the present invention is inhibited by the presence of the sugar immediately after in vivo administration, but the inhibition of the gelation of the collagen by the sugar is cancelled as the sugar gradually diffuses in the living body, and the collagen is estimated to restore its intrinsic property and undergo gelation. That is, the gelation of the sustained-release pharmaceutical composition of the present invention slowly progresses after administration to a living body, and a drug sustained-release action can be finally exhibited. The sustained-release pharmaceutical composition of the present invention is considered to have immediate-release property immediately after administration to a living body. As described above, the sustained-release pharmaceutical composition of the present invention has immediate-release property and sustained-release property, and has a controlled drug release rate.

In the present invention, the phrase "has immediate-release property" means that a pharmaceutical composition releases an effective amount of a drug in a period from immediately after administration to a given time (initial period). In the initial period, the pharmaceutical composition of the present invention releases a drug at a rate comparable to or slightly slower than that of a composition containing no collagen, and at a rate faster than that of a composition containing a collagen only and containing no sugar. For example, the pharmaceutical composition of the present invention can release a drug in an amount sufficient to provide a subject with an initial loading dose of the drug within a time of 5 hours or less, 2 hours or less, 1 hour or less, or about 30 minutes or less.

Further, in the present invention the phrase "has sustained-release property" means that a pharmaceutical composition releases a drug in a sustained manner for a long period as compared to a composition containing no collagen to maintain the concentration of the drug in vivo at an appropriate one. For example, the pharmaceutical composition of the present invention can release a drug in an amount sufficient to provide a living body of a subject with a continuous maintenance dose of the drug for the following period: after a lapse of 12 hours or more, after a lapse of 16 hours or more, or after a lapse of 1 day or more after administration and up to about 3 days, up to about 1 week, or up to about 1 month after administration; or after a lapse of 1 month or more and up to about 6 months after administration.

In addition, in the sustained-release pharmaceutical composition of the present invention, it is considered that a drug release rate can be more freely controlled by appropriately adjusting, for example, the concentrations, blending ratios, and blending order of ingredients including a drug, a collagen, and a sugar. In the sustained-release pharmaceutical composition of the present invention, an initial drug release amount can be increased as compared to a conventional composition containing a collagen only and containing no sugar, and immediate-release property can be imparted. For example, when a test is performed under the conditions described in Example 1 to be described later, a drug release rate can be regulated within such a range that a drug elution amount (cumulative drug release amount) 0 to 6 hours after the start of elution is increased by about 5 to 30% and a drug elution amount (cumulative drug release amount) 6 to 48 hours after the start of elution is increased by 30 to 50% as compared to a conventional composition containing a collagen only and containing no sugar. It should be noted that each of those numerical values is an example of an initial drug release rate (a time range in which immediate-release property is exhibited and a cumulative drug release amount in the time range) in the sustained-release pharmaceutical composition of the present invention, and the initial drug release rate in the present invention is not limited thereto and can be controlled by the kinds and concentrations of a drug, a sugar, and a collagen.

The pharmaceutical composition of the present invention is in a liquid form before administration to a body and has property of undergoing gelation after the administration. The gelation of the pharmaceutical composition of the present invention is probably due to a collagen. It is known that the gelation of the collagen generally occurs under physiological conditions. The physiological conditions mean the conditions of a temperature of 2 to 45° C., a pH of 4.0 to 10.0, and a salt concentration of 0.01 to 3.0 M. The pharmaceutical composition of the present invention is still in a liquid form and does not undergo gelation even when placed under physiological conditions before administered to a body. Further, the liquid form and gelated state in the present invention may be distinguished from each other by measuring a turbidity. For example, the turbidity may be confirmed by measuring an absorbance at 400 nm. The property of undergoing gelation means having such property that an absorbance at 400 nm increases, for example, such property that the absorbance increases to about 1.0, when a composition containing a collagen is placed under physiological conditions.

The sugar contained in the sustained-release pharmaceutical composition of the present invention is at least one kind of sugar selected from monosaccharides, disaccharides, trisaccharides, and tetrasaccharides. Examples of the monosaccharides include: pentoses such as xylose, arabinose, and ribose; hexoses such as glucose, mannose, galactose, fructose, and fucose; sugar alcohols such as inositol and erythritol; amino sugars such as glucosamine; and uronic acids such as glucuronic acid. Examples of the disaccharides include sucrose, maltose, lactose, trehalose, and isomaltose. Examples of the trisaccharides include raffinose. Examples of the tetrasaccharides include stachyose. The sugar contained in the sustained-release pharmaceutical composition of the present invention is preferably at least one kind of sugar selected from disaccharides and trisaccharides, more preferably a disaccharide. A disaccharide and a trisaccharide are preferred from the viewpoint of handleability in the preparation of the pharmaceutical composition as well. In the present invention, when the sustained-release pharmaceutical composition is produced by allowing a collagen to coexist with polysaccharides including penta- or more saccharides in place of at least one kind of sugar selected from monosaccharides, disaccharides, trisaccharides, and tetrasaccharides, it is considered that a drug sustained-release rate cannot be regulated because drug sustained-release property by the collagen is not substantially affected.

The concentration of the sugar in the sustained-release pharmaceutical composition of the present invention is one at which the sugar is capable of inhibiting gelation mediated by the collagen at a final concentration in the pharmaceutical composition, and is such a concentration that the pharmaceutical composition of the present invention does not undergo gelation even when placed under physiological conditions. In addition, the concentration of the sugar in the pharmaceutical composition of the present invention may be increased or decreased depending on the addition of other ingredients in the pharmaceutical composition, and is preferably adjusted to an isotonic concentration with respect to an osmotic pressure in vivo as a whole. For example, the concentration of the sugar is 0.01 to 3.0 M, preferably 0.05 to 1.0 M, still more preferably 0.1 to 0.5 M. When the concentration of the sugar is less than 0.01 M, there is a problem in that a gelation inhibiting effect is not obtained. When the concentration is more than 3.0 M, there is a problem in that the gelation of the collagen is completely inhibited and the composition does not exhibit drug sustained-release property.

It should be noted that, in the sustained-release pharmaceutical composition of the present invention, by changing the kind and concentration of the sugar, it is possible to regulate a drug release rate and to regulate a balance between immediate-release property immediately after administration to a living body and sustained-release property due to the gelation of the collagen. The balance between immediate-release property and sustained-release property may be regulated depending on, for example, the kind of the drug. For example, when the sustained-release pharmaceutical composition of the present invention contains a disaccharide or a trisaccharide, the composition has a relatively high ability to suppress the gelation of the collagen, and hence can realize a higher local concentration through drug release in an initial period after administration, which enables immediately effective drug release. Meanwhile, when the sustained-release pharmaceutical composition of the present invention contains a monosaccharide or a tetrasaccharide, the composition has a relatively low ability to suppress the gelation of the collagen, and hence can reduce a drug release rate as compared to a formulation containing a disaccharide or a trisaccharide. The concentration of the sugar in the sustained-release pharmaceutical composition of the present invention is as described above, and is exemplified by the following concentrations: preferably 0.05 M to 0.3 M in the case of a disaccharide; preferably 0.01 M to 0.3 M in the case of a trisaccharide; preferably 0.05 M to 0.5 M in the case of a monosaccharide; and preferably 0.05 M to 0.3 M in the case of a tetrasaccharide.

The collagen in the sustained-release pharmaceutical composition of the present invention may be any collagen as long as it can undergo gelation under physiological conditions. The collagen is distinguished from gelatin as a denatured product of the collagen. The collagen has a triple-helical structure formed of an assembly of three helical polypeptide chains, whereas gelatin does not have such structure. The triple-helical structure in the collagen is formed of molecules each including a repeating sequence of $(Gly-X-Y)_n$ (X and Y each represent any amino acid). The molecular weight of the collagen in the pharmaceutical composition of the present invention is 1 to 2,000 kDa, preferably 10 to 1,000 kDa, more preferably 100 to 500 kDa. When the molecular weight of the collagen is less than 1 kDa, for example, there is a problem in that the gelation of the collagen does not occur under physiological conditions. When the molecular weight is more than 2,000 kDa, for example, there is a problem in that the gelation occurs even under conditions other than the physiological conditions, which makes it difficult to handle the formulation. It should be noted that the molecular weight as used herein means a total molecular weight, and is generally measured by a GPC method or the like.

In the present invention, there may be used as the collagen, for example, atelocollagen obtained by treatment with a protease such as pepsin (Stenzel et al., Collagen as a biomaterial, Annual Review of Biophysics and Bioengineering, (1974) 3, 231) as well as various types of natural collagens. As the atelocollagen, there may be used atelocollagen derived from any of various living beings such as a chicken, cattle, a pig, and a human. Further, a chemically modified collagen, a collagen-like molecule in which synthetic polypeptides each including a repeating sequence of Gly-X-Y (X and Y each represent any amino acid) such as $(Pro-Hyp-Gly)_5$ form a triple helix, or the like may be used as long as it can undergo gelation under physiological conditions. For example, gelatin or a collagen peptide does not undergo gelation under physiological conditions, and hence is not preferred as the collagen to be used in the sustained-release pharmaceutical composition of the present invention.

The concentration of the collagen in the present invention may be any concentration as long as it is such a concentration that gelation occurs under physiological conditions at the final concentration in the pharmaceutical composition. For example, the concentration of the collagen is 0.01 to 30% by weight (% [w/v]), preferably 0.05 to 20% by weight (% [w/v]), more preferably 0.1 to 10% by weight (% [w/v]). When the concentration of the collagen is less than 0.01% by weight (% [w/v]), for example, there is a problem in that the gelation of the collagen does not occur. When the concentration is more than 30% by weight (% [w/v]), for example, there is a problem in that the sustained-release pharmaceutical composition of the present invention cannot be handled as a solution.

The blending ratio of the collagen to the sugar in the sustained-release pharmaceutical composition of the present invention has only to be such a blending ratio that the sugar is capable of inhibiting the gelation of the collagen. For example, with regard to the blending ratio of the collagen to the sugar, the weight (g) of the sugar with respect to 1 part by weight (1 g) of the collagen has only to be 1:0.005 to 1:5,000, and has only to be preferably 1:0.01 to 1:1,000, more preferably 1:0.02 to 1:500, still more preferably 1:0.1 to 1:100. When the weight (g) of the sugar with respect to 1 part by weight (1 g) of the collagen is less than 0.005, for example, there is a problem in that an effect of inhibiting gelation is not obtained. When the weight is more than 5,000, for example, there is a problem in that the gelation of the collagen is completely inhibited, and thus the composition does not exhibit drug sustained-release property. Further, it should be noted that the gelation may be inhibited at a higher level by increasing the weight (g) of the sugar with respect to 1 part by weight (1 g) of the collagen, to thereby produce a pharmaceutical composition having a high proportion of immediate-release property.

In the sustained-release pharmaceutical composition of the present invention, the collagen is present as a collagen solution by being dissolved in a medium. Any medium may be used as the medium as long as it satisfies a pH and a salt concentration under physiological conditions. For example, there may be used a medium such as purified water for injection, physiological saline, or a buffer (e.g., a physiological phosphate buffer, an acetate buffer, or a citrate buffer).

The sustained-release pharmaceutical composition of the present invention contains a drug as an active ingredient. The drug has only to be a physiologically active substance having an action of preventing and/or treating a disease or a pathologic condition. Examples of the drug include physiologically active substances having actions of promoting tissue regeneration and of promoting and enhancing a physiological action, and ones used as general pharmaceuticals such as an anti-cancer agent and an antibiotic. The drug may be any of a protein, a peptide, a glycoprotein, a polysaccharide, a nucleic acid, and a low-molecular-weight compound. Of those, a protein, a peptide, or a glycoprotein is preferred. In the present invention, the peptide is a molecule in which two or more amino acids are bound together, and the protein and the peptide have substantially the same meaning. The glycoprotein has a sugar chain bound to a protein. The protein as the drug in the present invention may be any protein, and for example, one having a molecular weight of 1 to 1,000 kDa may be used.

Examples of the protein, the peptide, and the glycoprotein include a fibroblast growth factor (FGF), an epidermal growth factor (EGF), a nerve growth factor (NGF), an insulin-like growth factor (IGF), a colony stimulating factor (CSF), a granulocyte-colony stimulating factor (G-CSF), a transforming growth factor (TGF), a vascular endothelial growth factor (VEGF), a growth hormone (GH), erythropoietin (EPO), a hepatocyte growth factor (HGF), a tumor necrosis factor (TNF-α), lymphotoxin (TNF-β), an interleukin, an interferon, insulin, parathyroid hormone (PTH), a platelet-derived growth factor (PDGF), a vaccine antigen, an antibody, lysozyme (cell wall digesting enzyme), serrapeptase (anti-inflammatory enzyme preparation), and Pronase (anti-inflammatory enzyme preparation). The FGF is preferably basic fibroblast growth factor (bFGF).

Examples of the nucleic acid include: a gene encoding an enzyme, a hormone, a cytokine, a colony stimulating factor, a coagulation factor, a regulatory protein, a transcription factor, a receptor, or a structural protein; and an antisense oligonucleotide, siRNA, miRNA, RNA, DNA, or aptamer targeting such gene and formed of a single-stranded or double-stranded nucleic acid formed of an oligonucleotide or an oligonucleoside.

The concentration of the drug in the sustained-release pharmaceutical composition of the present invention has only to be one sufficient to exhibit an action of preventing and/or treating a disease or a pathological condition in vivo of a subject (patient) to which the sustained-release pharmaceutical composition of the present invention is administered. The concentration of the drug has only to be comparable to the effective concentration of a pharmaceutical to be generally used. Further, the concentration may be a concentration at which it has been clarified that effectiveness is exhibited by the drug only. However, a case where the mixing with the collagen decreases or increases the concentration at which the effectiveness is exhibited as compared to the case of the drug only is also envisaged. The sustained-release pharmaceutical composition of the present invention is preferably topically used, and hence the concentration of the drug in the sustained-release pharmaceutical composition has only to be determined focusing on the local concentration of the drug.

The sustained-release pharmaceutical composition of the present invention may further contain a pharmaceutically acceptable carrier. When the sustained-release pharmaceutical composition of the present invention is an injectable injection, for example, a dispersant, a surfactant, a tonicity agent, a pH adjusting agent, a soothing agent, a stabilizer, a preservative, or a colorant may be used as the pharmaceutically acceptable carrier as necessary.

The sustained-release pharmaceutical composition of the present invention is preferably used parenterally as an injection. For example, the administration of the composition may be intradermal administration, subcutaneous administration, intramuscular administration, intracavity administration, or administration to an organ or a tissue. Further, the sustained-release pharmaceutical composition of the present invention may be administered to vertebrates (such as: fishes; amphibians; reptiles; birds including a chicken and the like; and mammals including a mouse, a rat, a rabbit, a cat, a dog, cattle, a pig, a horse, a goat, a sheep, a monkey, a human, and the like) as subjects.

When the drug is a physiologically active substance exhibiting an angiogenesis regulating action, the sustained-release pharmaceutical composition of the present invention may be used as an angiogenesis regulator. In the present invention, the angiogenesis regulation means an action of promoting and/or inhibiting angiogenesis. Examples of the physiologically active substance exhibiting an angiogenesis regulating action include FGF (preferably bFGF), PDGF, VEGF, HGF, G-CSF, fumagillin, bevacizumab, ranibizumab, a recombinant human monoclonal Fab antibody that neutralizes active forms of vascular endothelial growth factor A (VEGF-A)), cimetidine, celecoxib), azaspirene, and pegaptanib (nucleic acid pharmaceutical). Of those, bFGF is preferred.

When the angiogenesis regulator of the present invention is administered to a living body, the local concentration of the physiologically active substance exhibiting an angiogenesis regulating action as an active ingredient increases early and the substance can be released in a sustained manner over a long period and kept at an appropriate concentration. Hence, the angiogenesis regulator may be used for various treatment applications using an angiogenesis regulating action.

When the physiologically active substance exhibiting an angiogenesis regulating action is bFGF, the substance is released in an amount sufficient to provide a subject with an initial loading dose of bFGF within a time of 2 hours or less, 1 hour or less, 30 minutes or less, or about 10 minutes or less. It is meant that the angiogenesis regulator is released in an amount sufficient to provide a subject with a continuous maintenance dose of bFGF for a time of 12 hours or more, 16 hours or more, or 20 hours or more and up to about 24 hours, up to about 28 hours, or up to about 32 hours after administration. For example, the angiogenesis regulator can be prepared so that the final concentration of bFGF is 25 µg/mL, to thereby set the dosage (dose) of bFGF at the local site of a subject to about 100 to about 500 µg, preferably about 200 µg.

The angiogenesis regulator of the present invention may be applied to, for example, angiogenesis promotion, angiogenesis inhibition, tissue regeneration, wound healing, bone disease treatment, periodontal disease treatment, cartilage disease treatment, or cancer treatment. The angiogenesis regulator is preferably used for angiogenesis promotion or tissue regeneration. As a disease expected to improve its symptom through angiogenesis promotion and/or tissue regeneration by the angiogenesis regulator of the present invention, there are given vascular occlusive diseases and ischemic diseases concurrent to the vascular occlusion in general. Specifically, the disease is any of chronic arterial occlusive diseases in general and examples thereof include arteriosclerosis obliterans, Buerger's disease, diabetic gangrene, myocardial infarction, and angina pectoris.

The dosage of the angiogenesis regulator of the present invention may be appropriately adjusted depending on, for example, a disease to be treated and the age and body weight of a patient. For example, the dosage in terms of bFGF is generally selected from the range of about 0.01 to about 500 µg, preferably the range of about 1 to about 300 µg, per adult human patient, and can be injected into an affected site or a peripheral site thereof. Further, when the effect in single administration is insufficient, the administration may also be performed a plurality of times.

The sustained-release pharmaceutical composition of the present invention may be produced by mixing ingredients including a drug, a collagen, and a sugar at predetermined concentrations and blending ratios. In this case, the blending order of the drug, the collagen, and the sugar is not particularly limited, and for example, the composition may be produced by blending the ingredients in any of the following orders.

(1) A collagen is added to a mixture containing a drug and a sugar.
(2) A sugar is added to a mixture containing a drug and a collagen.
(3) A drug is added to a mixture containing a sugar and a collagen.

Further, it is considered that a drug release rate may be controlled more freely by appropriately adjusting the concentrations, the blending ratios, and the blending order.

In addition, the present invention also encompasses a sustained-release base, including: a collagen; and at least one kind of sugar selected from monosaccharides, disaccharides, trisaccharides, and tetrasaccharides. The sustained-release base means a solvent or base for the sustained-release pharmaceutical composition. The sustained-release pharmaceutical composition may be produced by adding a drug as an active ingredient to the sustained-release base of the present invention, followed by mixing.

In the present invention, at least one kind of sugar selected from monosaccharides, disaccharides, trisaccharides, and tetrasaccharides can be allowed to be present in a pharmaceutical composition containing a drug and a collagen, to thereby impart immediate-release property and sustained-release property to the pharmaceutical composition. Thus, there is also provided a method of controlling a drug release rate.

In the method of manufacturing a sustained-release pharmaceutical composition or method of controlling a drug release rate of the present invention, in consideration of the gelation of the collagen, in a state in which the sugar is absent, a blending operation is preferably performed at a temperature at which the collagen is not denatured, preferably at a low temperature of 2 to 10° C., and in a state in which the sugar is present, a mixing operation may be performed at 0 to 50° C., more preferably 10 to 40° C.

EXAMPLES

Hereinafter, the present invention is specifically described by way of Reference Examples and Examples showing the contents of the present invention. However, the present invention is by no means limited thereto.

Reference Example 1

Spectroscopic Evaluation of Influence of Sugar on Gelation Ability of Collagen Solution Specifically, a sucrose solution was added to a collagen solution (pH 7.4, final concentration: 3% [w/v]) (product name: KOKEN ATELOCOLLAGEN IMPLANT) so that the final concentration was 0, 0.01, or 0.25 M, followed by mixing. The mixed solution was measured for its time-dependent change in absorbance at 400 nm with a spectrophotometer while being heated at 37° C.

FIG. 1 shows the results. In the figure, "a" shows the result in the case of a collagen only, "b" shows the result in the case of a blend of a collagen and 0.01 M sucrose, and "c" shows the result in the case of a blend of a collagen and 0.25 M sucrose. The collagen solution to which no sucrose was added underwent gelation in about 10 minutes. In each of the collagen solutions to which sucrose was added, its gelation was delayed in a sucrose concentration-dependent manner.

Example 1

Confirmation of Influence of Sugar on Drug Release from Collagen

The influence of a sugar on drug release from a collagen was confirmed through use of lysozyme (final concentration: 2 mg/mL) (Sigma-Aldrich Corporation) as a drug.

Lysozyme was dissolved in a physiological buffer (PBS, pH 7.4) containing sucrose (final concentration: 0.05 M) or a physiological buffer containing no sucrose. After that, the solution and an atelocollagen solution (final concentration: 3% [w/v]) (product name: KOKEN ATELOCOLLAGEN IMPLANT) were mixed and formulated. The resultant formulation was gently added to a solution containing PBS as an external liquid in a test tube, followed by heating at 37° C., and the amount of the lysozyme released into the external liquid in a time-dependent manner was measured by HPLC (system integrator: C-R7A [Shimadzu Corporation], system controller: SCL-6B [Shimadzu Corporation], pump: LC-9A [Shimadzu Corporation], degasser: ERC-3522 [Elma], detector: SPC-6AV [Shimadzu Corporation], column: Cosmosil C18-AR [NACALAI TESQUE, INC.]).

Figure 2:
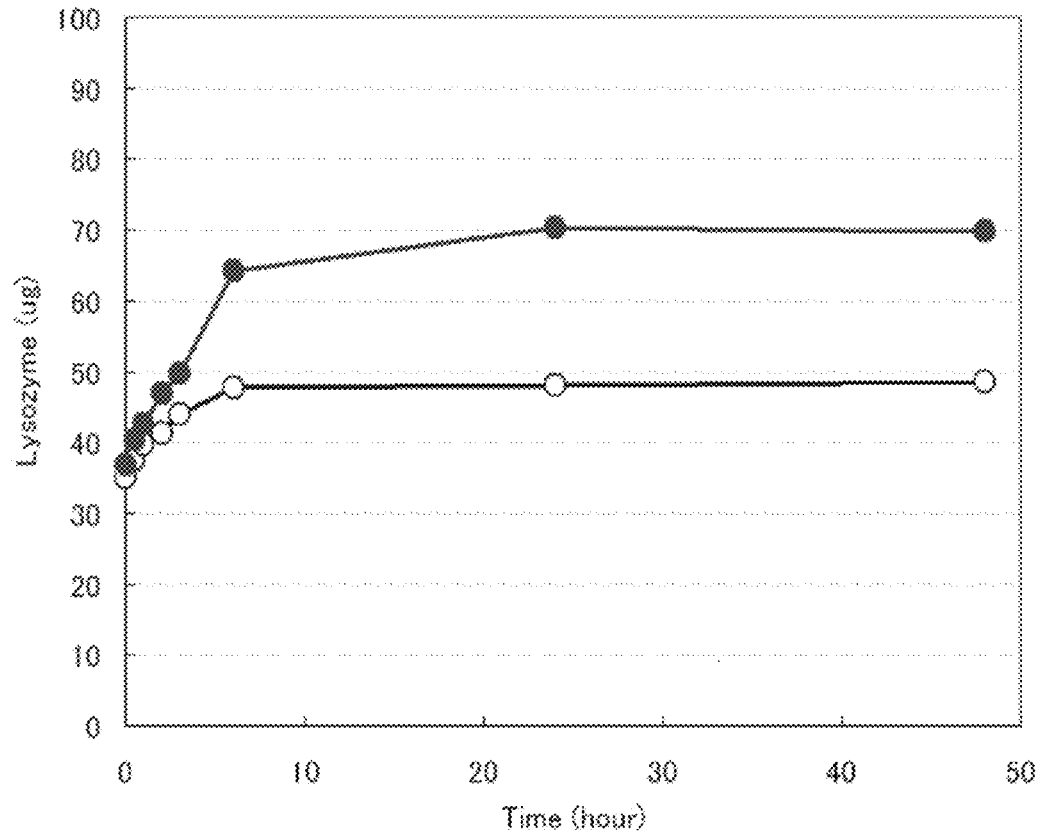
[FIG. 2] A graph showing the results of confirmation of the influence of sugar addition on a drug release rate in vitro. In the figure, the filled circle shows the result in the case where sucrose is present, and the open circle shows the result in the case where sucrose is absent (Example 1).

Conditions for the measurement were as follows:
Initial eluent: 30% acetonitrile solution containing 0.1% triethylamine (TEA)
Final eluent: concentration-gradient elution with 45% acetonitrile solution containing 0.1% TEA
rate: 1 mL/min
Elution time: 30 minutes
Detection wavelength: 220 nm FIG. 2 shows the results. In the figure, the open circle shows the result in the case where sucrose is absent, and the filled circle shows the result in the case where sucrose is present. The amount of the lysozyme released into the external liquid was found to be large in the case of containing sucrose as compared to the case of containing no sucrose. The results revealed that the addition of the sugar accelerated drug release from the collagen solution, resulting in an increase in initial drug release amount.

Example 2

Confirmation of Influence of Formulation Procedure on In Vivo Gelation of Collagen The following three kinds of ingredients were mixed in different orders and formulated as shown in the following items a) to c): lysozyme (MW: 14 kDa) (final concentration: 2 mg/mL); sucrose (final concentration: 0.25 M); and atelocollagen (final concentration: 3% [w/v]) (product name: KOKEN ATELOCOLLAGEN IMPLANT).

a) (P+S)+AC formulation: First, Lysozyme and sucrose were mixed, and next atelocollagen was added to prepare a formulation.
b) (P+AC)+S formulation: First, lysozyme and atelocollagen were mixed, and next sucrose was added to prepare a formulation.
c) (S+AC)+P formulation: First, sucrose and atelocollagen were mixed, and next lysozyme was added to prepare a formulation.

An AC formulation formed only of atelocollagen was used as a control formulation.

100 µL of each of the formulations according to the above-mentioned items a) to c) were administered to the dorsal subcutis of mice (DDY, female, 20-week-old). The presence or absence of gelation of atelocollagen in vivo was confirmed 24 hours after the administration to the mice.

Figure 3:
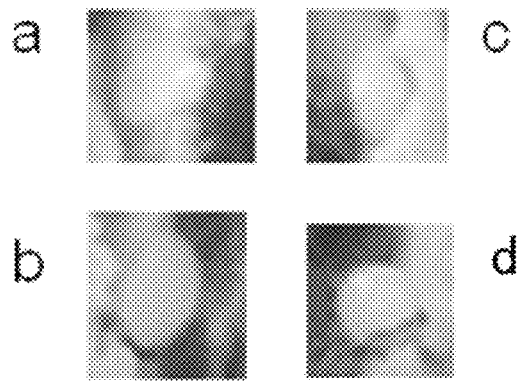
[FIG. 3] Photographs showing the results of confirmation of an influence of the blending order of respective ingredients on collagen gelation in vivo.

FIG. 3 show the states of the respective formulations in vivo after 24 hours. FIGS. 3a to 3c show the results of the respective formulations according to the above-mentioned items a) to c), and FIG. 3d shows the result of the control formulation. Each of the formulations according to the above-mentioned items a) to c) and the control formulation formed a white gel in the dorsal subcutis of the mice. The results revealed that the order of the addition and mixing of the sugar did not have any influence on the in vivo gelation of the collagen, and each of the formulation procedures resulted in the in vivo gelation of the collagen, in other words, the formation of a form as a release carrier for a drug.

Example 3

Confirmation of Influence of Formulation Procedure on Drug Release Rate

The following three kinds of ingredients were mixed in different orders and formulated as shown in the following items a) to d): lysozyme (MW: 14 kDa); sucrose; and atelocollagen (product name: KOKEN ATELOCOLLAGEN IMPLANT). Each of the formulations was administered to dorsal subcutis of mice, and 1 hour later, the release amount of lysozyme was measured.

a) (P+S)+AC formulation: First, lysozyme and sucrose were mixed, and next atelocollagen was added to prepare a formulation.
b) (P+AC)+S formulation: First, lysozyme and atelocollagen were mixed, and next sucrose was added to prepare a formulation.
c) (S+AC)-FP formulation: First, sucrose and atelocollagen were mixed, and next lysozyme was added to prepare a formulation.
d) AC+P formulation: Atelocollagen and lysozyme were mixed to prepare a formulation.

Each of the formulations was prepared so that the final concentrations of lysozyme, sucrose, and atelocollagen were 5 mg/mL, 0.25 M, and 3% [w/v], respectively.

100 µL of each of the formulations according to the above-mentioned items a) to d) were administered to the dorsal subcutis of mice. One hour later, the formulation that underwent gelation at a body temperature was taken out, and the amount of the lysozyme remaining in the gel was measured by HPLC to calculate the release amount of the lysozyme.

Figure 4:
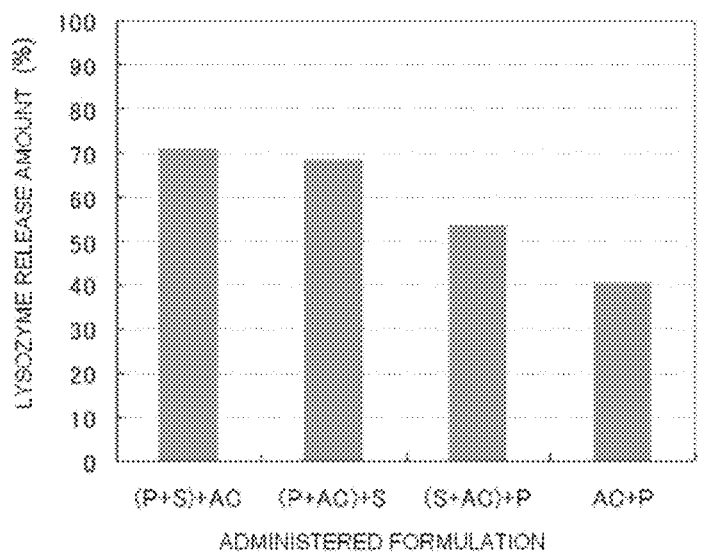
[FIG. 4] A graph showing the results of confirmation of an influence of a blending order on a drug release rate in vivo (Example 3).

FIG. 4 shows the results. The release amount of the lysozyme varied depending on a change in mixing procedure. The results revealed that a sustained-release characteristic was changed in vivo by changing the mixing procedure of a collagen, a drug, and a sugar. It should be noted that each of the formulations 1 hour after the administration to the dorsal subcutis of the mice underwent gelation and maintained a form as a sustained-release carrier for a drug.

Example 4

Confirmation of Influence of Molecular Weight of Drug on In Vivo Gelation of Collagen The following three kinds of ingredients were formulated: a drug as any of various proteins (final concentration: 10 mg/mL) shown in Table 1 below; sucrose (final concentration 0.25 M); and atelocollagen (final concentration: 3% [w/v]) (product name: KOKEN ATELOCOLLAGEN IMPLANT). In the same manner as the technique of Example 2c), the formulation was performed by: dissolving sucrose in a physiological buffer; mixing the solution with an atelocollagen solution; and adding a protein dissolved in a physiological buffer.

TABLE 1

| Used proteins and their molecular weights | |
|---|---|
| Protein | MW (kDa) |
| Transferrin (T1428, Sigma Aldrich) | 76 |
| Phosphorylase b (P6635, Sigma Aldrich) | 97 |
| Myosin heavy chain (M7659, Sigma Aldrich) | 220 |
| Ferritin type I (F4503, Sigma Aldrich) | 440 |
| Thyrogloblin (T1001, Sigma Aldrich) | 669 |

100 µL of each of the formulations containing the proteins shown in Table 1 were administered to one site of the dorsal subcutis of mice (ICR, male, 8-week-old, body weight: 27 to 29 g). The presence or absence of in vivo gelation of the collagen was confirmed 24 hours after the administration.

Figure 5:
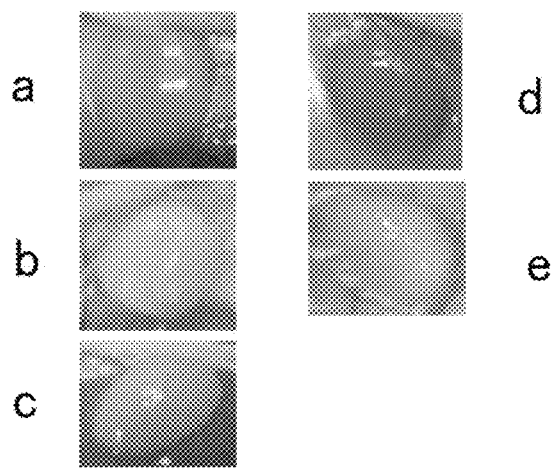
[FIG. 5] Photographs showing the results of confirmation of an influence of the kind of a drug on collagen gelation in vivo.

FIG. 5 show the states of the respective formulations in vivo after 24 hours. FIG. 5a shows the result of transferrin, FIG. 5b shows the result of phosphorylase b, FIG. 5c shows the result of myosin heavy chain, FIG. 5d shows the result of ferritin type I, and FIG. 5e shows the result of thyrogloblin. Each of the formulations formed a gel in the dorsal subcutis of the mice. The results revealed that the molecular weight of the drug, in particular, the protein did not have any influence on the gelation of the collagen, and the in vivo gelation of the collagen occurred in each of the formulations.

Example 5

Confirmation of Effect of Formulation of Present Invention 1

The following three kinds of ingredients were sequentially mixed: bFGF (MW: 17 kDa) (final concentration: 2 mg/mL) used as a drug; sucrose (final concentration: 0.25 M); and atelocollagen (final concentration: 3% [w/v]) (product name: KOKEN ATELOCOLLAGEN IMPLANT). 20 µL of the mixed formulation were administered to the dorsal subcutis of mice (C57BL/6 [SLC], female, 7-week-old). The state of the tissue at the administration site after 3 weeks was macroscopically observed.

Figure 6:
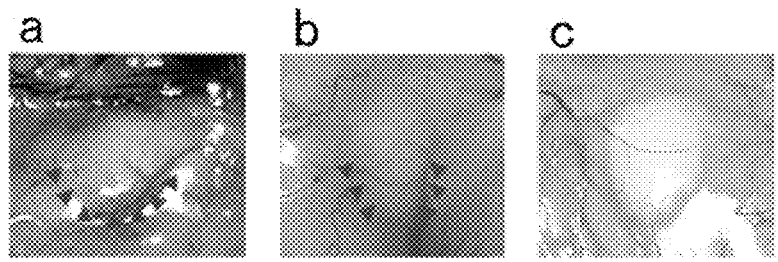
[FIG. 6] Photographs showing the results of confirmation of an in vivo angiogenesis promoting action of a sustained-release pharmaceutical composition containing bFGF as a drug.

FIG. 6 show the results. In the case of administering a formulation containing sucrose (FIG. 6a), the periphery of the blood vessel at the administration site was found to become reddish (arrows), suggesting capillary angiogenesis. On the other hand, in the case of administering a formulation containing no sucrose (FIG. 6b), no clear redness was observed in the periphery of the administration site (arrows), suggesting that angiogenesis was delayed as compared to the formulation containing sucrose. In the case of administering a collagen solution only as a control, no capillary angiogenesis was observed as with the formulation containing no sucrose (FIG. 6c). Such difference in effect of bFGF in the subcutis (difference between FIGS. 6a and 6b) was considered to be due to a difference in time for which bFGF was released from the formulation in the collagen gelation process, and it was estimated that the release of bFGF was rapid and capillary angiogenesis was accelerated in the formulation containing sucrose.

Example 6

Confirmation of Effect of Formulation of Present Invention 2

1) Preparation of Formulation

A collagen solution (final concentration: 3% [w/v]) (product name: KOKEN ATELOCOLLAGEN IMPLANT (KOKEN CO., LTD.)) was added to a solution of bFGF containing white soft sugar (product name: FIBLAST Spray (KAKEN PHARMACEUTICAL CO., LTD.)) to prepare a formulation containing 1.0 mg/mL bFGF.

2) Production of Animal Model of Hindlimb Ischemia 34-week-old mice (C3H/He, male, Japan SLC, Inc.) were divided into two groups (n=10) and acclimatized under the environment of a room temperature of 19.5 to 26.4° C., a humidity of 34.5 to 75.4%, light/dark periods of 12 hours each, and feeding ad libitum.

Under 0.5 to 4% isoflurane anesthesia, the mice were fixed in the dorsal position, the thigh of the right hindlimb was incised, and the femoral artery on the central and peripheral sides and the saphenous artery on the periphery side were each ligated with a suture to block the blood circulation. A penicillin G potassium solution was dropped and the incised site was sutured.

3) Administration of Formulation to Animal Model of Hindlimb Ischemia

After the production of a mouse model of hindlimb ischemia, the formulation was administered with an injector to five sites of the muscle of the right ischemic hindlimb in an amount of 20 μL per site so that the dosage was 100 μg of bFGF per animal.

4) Measurement of Hindlimb Blood Flow Rate

The recovery of blood flow at the hindlimb ischemic site was evaluated through use of a laser doppler blood flow imager (OZ-1, OMEGAWAVE, INC.) 4 weeks after the administration of the formulation.

Under 0.5 to 4% isoflurane anesthesia, the mice were fixed in the dorsal position, and blood flow rates were measured at the right hindlimb (ischemic limb) and the left hindlimb (normal limb) to calculate a blood flow rate of ischemic limb/normal limb.

The results were expressed as mean±standard deviation (S.E.), and a significant difference ($p<0.05$) was evaluated by the Student's t test.

Figure 7:
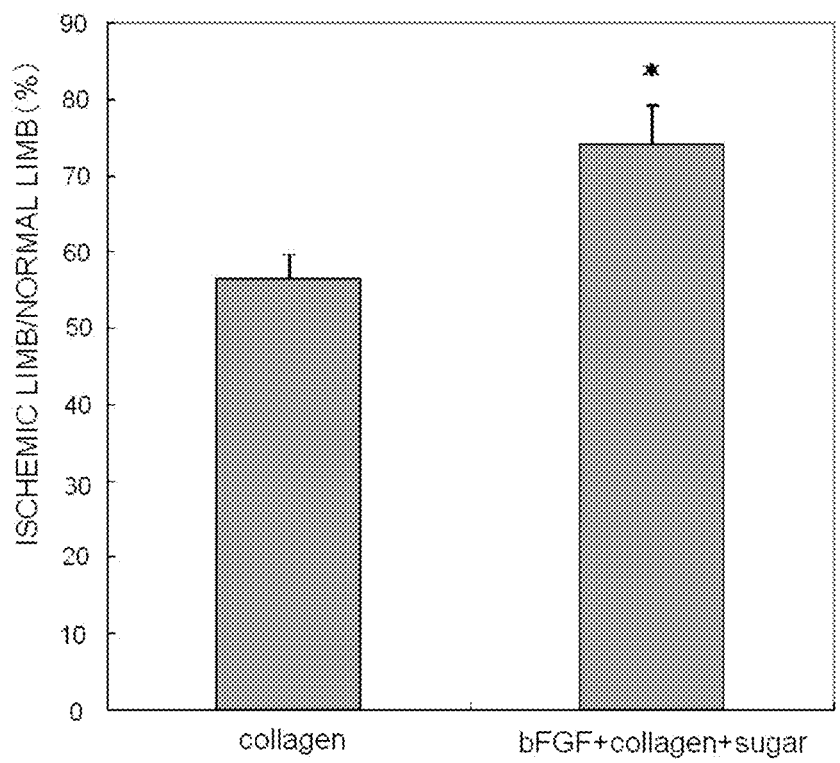
[FIG. 7] A graph showing the results of confirmation of drug efficacy of a sustained-release pharmaceutical composition containing bFGF as a drug on a mouse model of hind-limb ischemia (Example 6).

FIG. 7 shows the results. In the experiment using a mouse model of hindlimb ischemia, the blood flow rate was significantly recovered in a group in which the formulation containing sucrose was administered as compared to a group in which the collagen was administered as a control.

Example 7

Confirmation of Effect of Formulation of Present Invention 3

In order to confirm the effect of the formulation of the present invention, phase I and II clinical trials were performed as described below.

1) Subject

Subjects were cases who were diagnosed as negative for an intradermal reaction for bFGF-containing atelocollagen (AC) after giving informed consent out of patients with Fontaine stages III and IV who had lower extremity peripheral vascular disease with pain at rest or ischemic ulcer and necrosis and who did not show any improvement in clinical symptom even after subjected to any medical and surgical treatment. No age limit was set.

Patients excluded from the trials were patients who had experienced a lower extremity revascularization procedure (surgical bypass procedure, PTA) within 3 months, patients who had severe cardiac dysfunctions such as angina pectoris, myocardial infarction, and congestive heart failure, patients who had collagen disease, malignant neoplasm, infectious diseases, and diabetic retinopathy, pregnant women, and patients who were diagnosed as positive in an intradermal reaction for an atelocollagen solution.

Table 2 below shows the patients as the subjects of this example.

TABLE 2

| Cases | | | | |
|---|---|---|---|---|
| | Age | Gender | Fontaine | Disease |
| 1 | 41 | Male | III | Buerger's disease |
| 2 | 87 | Female | III | Peripheral arterial disease |

Buerger's disease (Synonym: Thromboangiitis obliterans): TAO
Peripheral arterial disease: PAD 2) Method Under lumbar epidural anesthesia, 3% [w/v] atelocollagen (AC) (product name: KOKEN ATELOCOLLAGEN IMPLANT (KOKEN CO., LTD.)) containing 200 μg of bFGF containing white soft sugar (product name: FIBLAST Spray (KAKEN PHARMACEUTICAL CO., LTD.)) was injected into the gastrocnemius muscle of ischemic lower extremity (100 μL×40 sites). No placebo or untreated group was set.

3) Evaluation

On week 4 and month 6, the atelocollagen solution containing 200 μg of bFGF was evaluated for its safety and therapeutic effect. Primary endpoint: the safety was confirmed as the primary endpoint. Secondary endpoint: Evaluations were performed from the two viewpoints of primary outcome assessment and secondary outcome assessment as the secondary endpoint.

Primary outcome assessment (pain at rest, ankle-brachial blood pressure index (ABI), 6-minute walk distance)

Secondary outcome assessment (transcutaneous oxygen pressure ($TcO_2$), skin perfusion pressure (SPP))

Specifically, evaluations were performed as described below.

Primary Outcome (i) Evaluation of Pain at Rest

Through use of a visual analogue scale (VAS) method, a pain at the time of measurement was evaluated by defining a maximum pain and no pain as 10 and 0, respectively.

(ii) 6-Minute Walk Distance

A distance that a patient was able to walk in 6 minutes (including a break therein, provided that no chair or the like was used during the break) was measured in the corridor of a hospital ward.

(iii) Ankle-Brachial Blood Pressure Index: ABI

The index was calculated from the ratio of a brachial blood pressure to an ankle blood pressure (brachial blood pressure/ankle blood pressure).

Secondary Outcome (i) Measurement of Transcutaneous Oxygen Partial Pressure (Transcutaneous Oxygen Pressure: $TcO_2$)

The skin was heated to 43.5° C. in advance, and the measurement was performed by attaching a probe to the frontal skin about 10 cm away from the tibial tuberosity toward the periphery side.

(Results)

Figure 8:
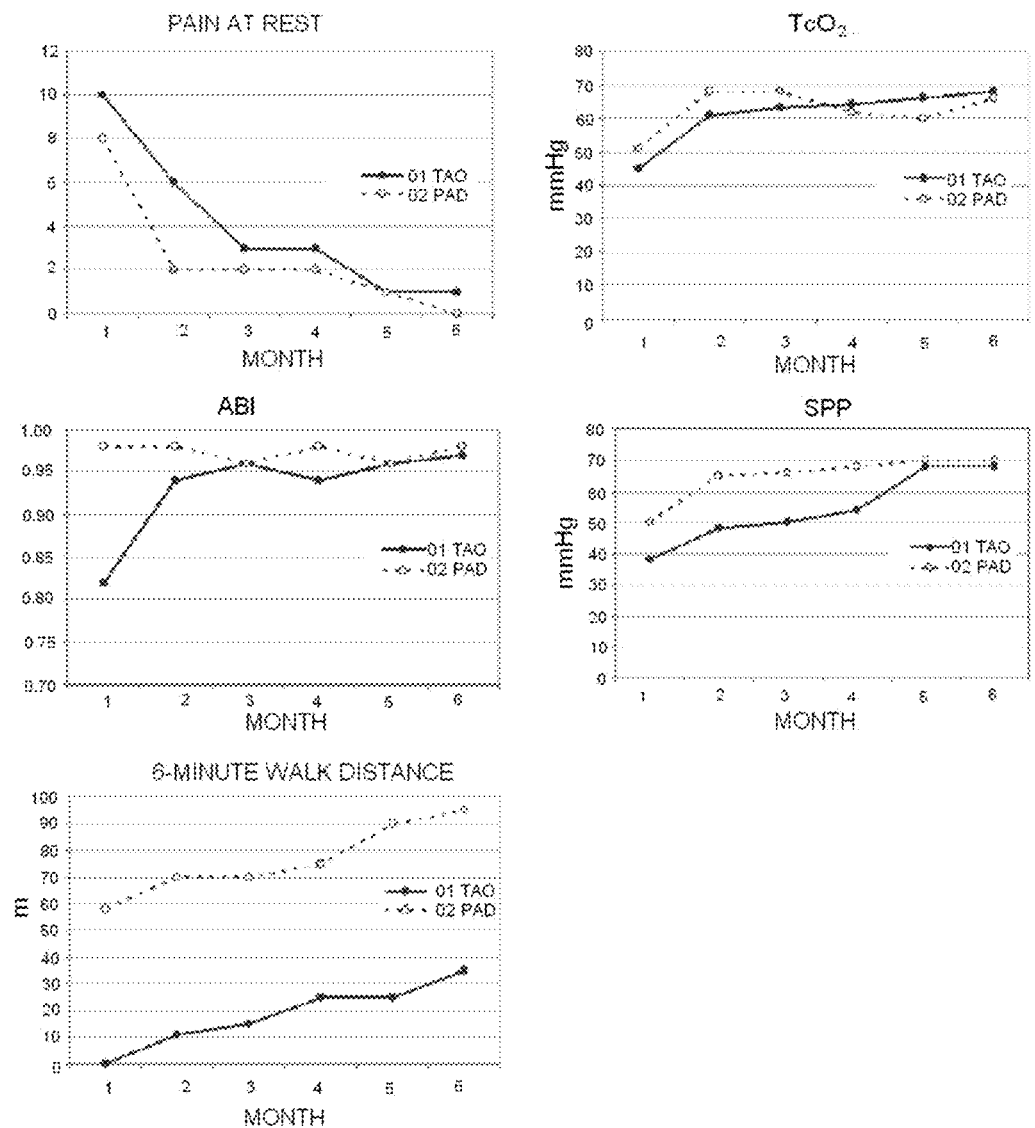
[FIG. 8] Graphs showing the results of phase I and II clinical trials performed for a sustained-release pharmaceutical composition containing bFGF as a drug (Example 7).

FIG. 8 show the results. Both the patients shown in Table 2 did not show any change during a hospitalization period of 4 days, in systemic symptom, blood, and urine examination, and were discharged from the hospital on schedule. No adverse event due to the administration of the formulation was found. In each of the patients, the pain at rest was improved in a time-dependent manner after the administration of the formulation as compared to before the treatment. With regard to the ABI, an improving effect was found in the patient with Buerger's disease showing a low value for the index. With regard to the 6-minute walk distance, an improving effect was found as compared to before the treatment in each of the patients. With regard to each of $TcO_2$ and SPP, an improving effect was found after the administration of the formulation.

Reference Example 2

Spectroscopic Evaluation of Influences of Sugar on Gelation Abilities of Various Collagen Solutions The influences of a sugar on the gelation abilities (fibrillogenic abilities) of various collagen solutions were investigated.

First, various collagens were each diluted to 0.2% [w/v] with 1 mM HCl. The various collagens used were as follows.
Type I atelocollagen (3.5% KAI: bovine, Lot. 1-107, pH 7)
Type I atelocollagen (3% KAI: porcine, stock of the laboratory, pH 7)
Type II atelocollagen (CL-22, Lot. 622052, pH 3)
Type III atelocollagen (NIP, 0.3% PSC-3-100-20, Lot. BSP310G001, 5 mM acetic acid)
Type I native collagen (1% 1-AC, Lot. 6002173, pH 3)
Shark atelocollagen (produced in the laboratory, powder, stored at −30° C.)

Distilled water (OTSUKA DISTILLED WATER, Cat. 1324, Lot. 0J90N), 2.5 M sucrose (Wako Pure Chemical Industries, Ltd., Cat. 196-00015, Lot. CKM1674), 100 mg/mL lysozyme (Tokyo Chemical Industry Co., Ltd., Cat. L072), and 10×PBS (DULBECCO'PBS, Dainippon Sumitomo Pharma Co., Ltd., Cat. 28-103-05 FN, Lot. 896458) were added to each of the various collagen solutions at 0.2% [w/v] to prepare a solution having final concentrations of 0.2% [w/v] collagen/0.25 M sucrose/10 mg/mL lysozyme/1× PBS. At this time, the ingredients were added so that the collagen, distilled water, sucrose, lysozyme, and PBS were mixed in this order.

100 µl of each of the prepared samples were added to a 96-well microplate and measured for its time-dependent change in absorbance at 400 nm (measurement interval: 30 seconds, measurement time: 3 hours) with an optical absorption microplate reader (TECAN, SUNRISE Thermo RC-R) while heated at 37° C. An average of the measured values (n=3) at the respective times was calculated.

Figure 9:
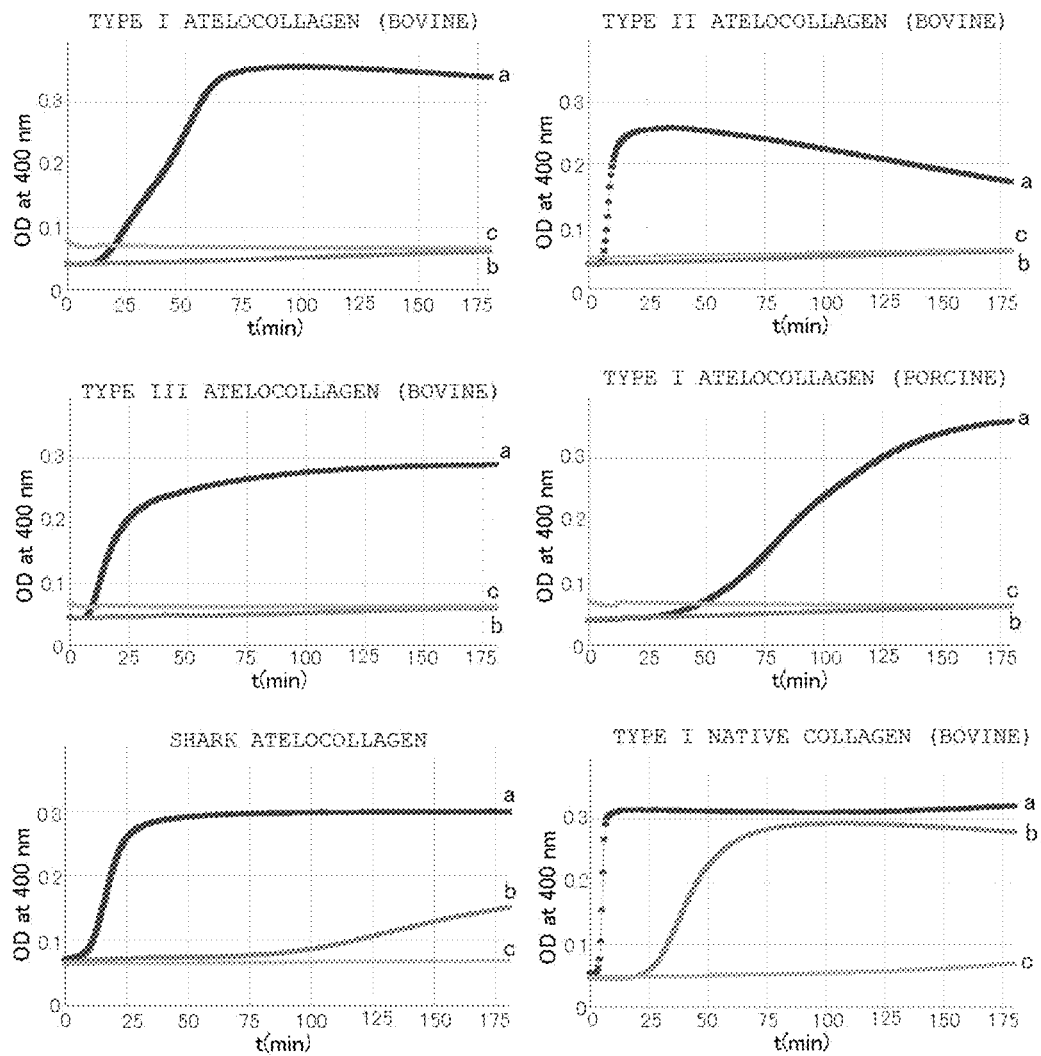
[FIG. 9] Graphs showing the results of confirmation of influences of sugar addition on the gelation of various collagens in vitro. In the figures, "a" shows the result of a formulation containing no lysozyme and no sucrose and containing a collagen only at 0.1% [w/v], "b" shows the result of a formulation containing no lysozyme and containing 0.25 M sucrose and a collagen at 0.1% [w/v], and "c" shows the result of a formulation containing 10 mg/mL lysozyme, 0.25 M sucrose, and a collagen at 0.1% [w/v] (Reference Example 2).

FIG. 9 shows the results. In the figures, "a" shows the result of a formulation containing no lysozyme and no sucrose and containing a collagen only at 0.1% [w/v], "b" shows the result of a formulation containing no lysozyme and containing 0.25 M sucrose and a collagen at 0.1% [w/v], and "c" shows the result of a formulation containing 10 mg/mL lysozyme, 0.25 M sucrose, and a collagen at 0.1% [w/v]. The results revealed that the addition of the sugar suppressed gelation in various collagen solutions containing type I, II, and III atelocollagens, type I native collagen, and shark atelocollagen.

Reference Example 3

Spectroscopic Evaluation of Influences of Various Sugars on Gelation Ability of Collagen Solution (1) The kind and concentration of a sugar to be added were changed, and an ability of the sugar to suppress the gelation of a collagen solution was confirmed by measuring a fibrillogenesis time.
The collagen was prepared so that the final concentration was 3% [w/v]. KAI (pH 7, PB buffer) was used as the collagen. The kinds and final concentrations of the used sugars are as described below.

(i) Monosaccharide: Glucose or Fructose
0.05, 0.125, 0.25, 0.5 M
(ii) Disaccharide: sucrose or maltose
0.05, 0.125, 0.25 M
(iii) Trisaccharide: raffinose
0.05 M
(iv) Tetrasaccharide: stachyose
0.05, 0.125 M It should be noted that, in this reference example, measurements were carried out without degassing.

Figure 10:
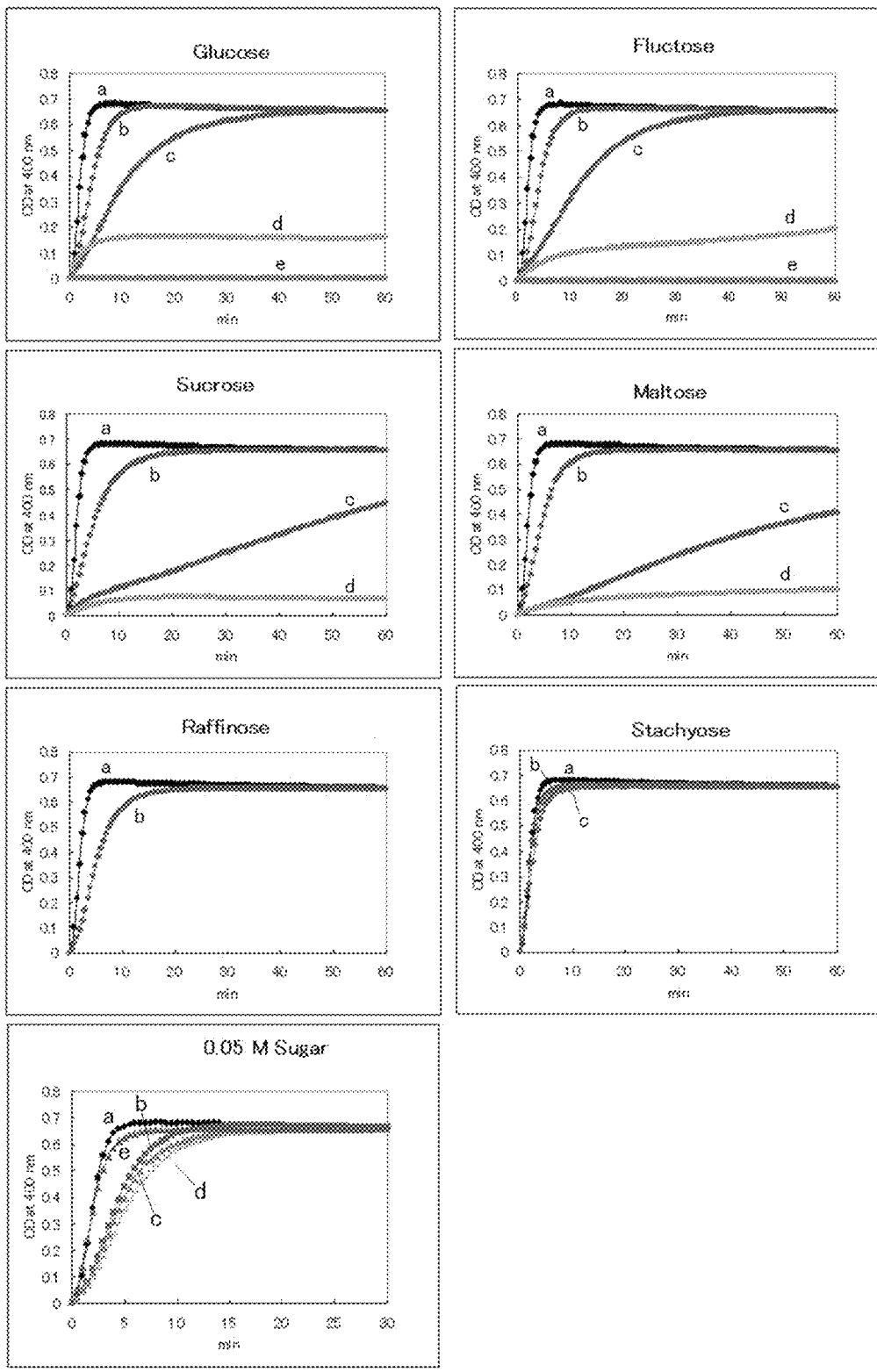
[FIG. 10] Graphs showing the results of confirmation of influences of addition of various sugars on collagen gelation in vitro. In the graphs of glucose and fructose, "a" shows the result of a formulation containing no sugar, "b" shows the result of a formulation containing a sugar at a concentration of 0.05 M, "c" shows the result of a formulation containing a sugar at a concentration of 0.125 M, "d" shows the result of a formulation containing a sugar at a concentration of 0.25 M, and "e" shows the result of a formulation containing a sugar at a concentration of 0.5 M. In the graphs of sucrose and maltose, "a" shows the result of a formulation containing no sugar, "b" shows the result of a formulation containing a sugar at a concentration of 0.05 M, "c" shows the result of a formulation containing a sugar at a concentration of 0.125 M, and "d" shows the result of a formulation containing a sugar at a concentration of 0.25 M. In the graph of raffinose, "a" shows the result of a formulation containing no sugar, and "b" shows the result of a formulation containing a sugar at a concentration of 0.05 M. In the graph of stachyose, "a" shows the result of a formulation containing no sugar, "b" shows the result of a formulation containing a sugar at a concentration of 0.05 M, and "c" shows the result of a formulation containing a sugar at a concentration of 0.125 M. In the graph showing a comparison among the sugars at 0.05 M, "a" shows the result of a formulation containing no sugar, "b" shows the result of a formulation containing glucose, "c" shows the result of a formulation containing maltose, "d" shows the result of a formulation containing raffinose, and "e" shows the result of a formulation containing stachyose (Reference Example 3).

FIG. 10 show the results. In the graphs of glucose and fructose, "a" shows the result of a formulation containing no sugar, "b" shows the result of a formulation containing a sugar at a concentration of 0.05 M, "c" shows the result of a formulation containing a sugar at a concentration of 0.125 M, "d" shows the result of a formulation containing a sugar at a concentration of 0.25 M, and "e" shows the result of a formulation containing a sugar at a concentration of 0.5 M. In the graphs of sucrose and maltose, "a" shows the result of a formulation containing no sugar, "b" shows the result of a formulation containing a sugar at a concentration of 0.05 M, "c" shows the result of a formulation containing a sugar at a concentration of 0.125M, and "d" shows the result of a formulation containing a sugar at a concentration of 0.25 M. In the graph of raffinose, "a" shows the result of a formulation containing no sugar, and "b" shows the result of a formulation containing a sugar at a concentration of 0.05 M. In the graph of stachyose, "a" shows the result of a formulation containing no sugar, "b" shows the result of a formulation containing a sugar at a concentration of 0.05 M, and "c" shows the result of a formulation containing a sugar at a concentration of 0.125 M. In the graph showing a comparison among the sugars at 0.05 M, "a" shows the result of a formulation containing no sugar, "b" shows the result of a formulation containing glucose, "c" shows the result of a formulation containing maltose, "d" shows the result of a formulation containing raffinose, and "e" shows the result of a formulation containing stachyose. In the case of adding a monosaccharide and a disaccharide, the gelation of the collagen was suppressed in a concentration-dependent manner. Further, even in the case of changing the kind of the sugar, the suppression of the gelation was able to be confirmed in a concentration-dependent manner. Also in the case of adding a trisaccharide, the fibrillogenesis time was found to be delayed as compared to the case of adding no sugar. However, in the case of a tetrasaccharide, the delay of the fibrillogenesis was hardly confirmed in the 3% [w/v] collagen solution.

(2) The influence of a tetrasaccharide on a gelation ability was confirmed in the same manner as in the above-mentioned method (1) except that: the concentration of the collagen was changed to 0.4% [w/v]; and KS collagen (pH 3) adjusted to pH 7 with a neutralization liquid (7% [w/v] $Na_2HPO_4$, 0.9% [w/v] NaCl) was used as the collagen solution. 0.05 M stachyose was used as the tetrasaccharide in the same manner as in the method (1).

Figure 11:
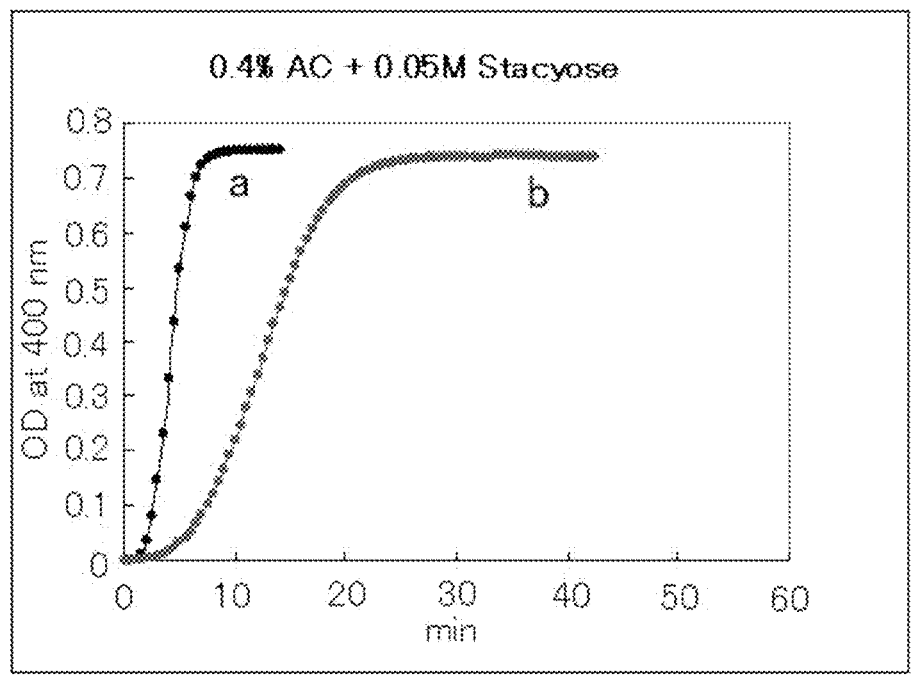
[FIG. 11] A graph showing the result of confirmation of an influence of addition of stachyose (tetrasaccharide) on collagen gelation in vitro. In the figure, "a" shows the result of a formulation containing no stachyose, and "b" shows the result of a formulation containing stachyose (Reference Example 3).

FIG. 11 shows the results. In the figure, "a" shows the result of a formulation containing no stachyose, and "b" shows the result of a formulation containing stachyose. In the case of adding the tetrasaccharide, the fibrillogenesis time of the collagen solution was delayed. Thus, it was able to be confirmed that the tetrasaccharide suppressed the fibrillogenesis of the collagen solution. The tetrasaccharide is considered to have a low fibrillogenesis suppressing effect as compared to the monosaccharide, the disaccharide, and the trisaccharide.

Reference Example 4

Spectroscopic Evaluation of Influences of Various Sugars on Gelation Ability of Collagen Solution The kind and concentration of a sugar to be added were changed, and an ability of the sugar to suppress the gelation of a collagen solution was confirmed by measuring a fibrillogenesis time.

Figure 12:
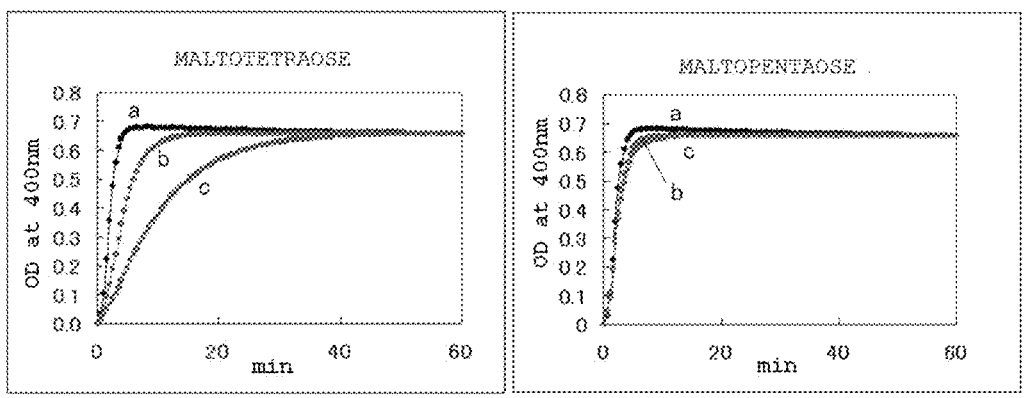
[FIG. 12] Graphs showing the results of confirmation of influences of addition of maltotetraose (tetrasaccharide) and maltopentaose (pentasaccharide) on collagen gelation in vitro. In the figures, "a" shows the result of a formulation containing no sugar, "b" shows the result of a formulation containing a sugar at 0.05 M, and "c" shows the result of a formulation containing a sugar at 0.125 M (Reference Example 4).

The collagen was prepared so that the final concentration was 3% [w/v]. KAI (pH 7, PB buffer) was used as the collagen. The kinds and final concentrations of the used sugars are as described below.
(i) Tetrasaccharide: maltotetraose
  0.05, 0.125 M
(ii) Pentasaccharide: maltopentaose
  0.05, 0.125 M FIG. 12 show the results. In the figures, "a" shows the result of a formulation containing no sugar, "b" shows the result of a formulation containing a sugar at 0.05 M, and "c" shows the result of a formulation containing a sugar at 0.125 M. Maltotetraose exhibited a fibrillogenesis suppressing effect comparable to that of the monosaccharide. In the case of adding maltopentaose, substantially no delay of the fibrillogenesis time was able to be confirmed in the 3% [w/v] collagen solution.

Reference Example 5

Spectroscopic Evaluation of Influences of Sugars on Gelation Abilities of Collagen Solutions Having Various Concentrations The influence of a concentration ratio between a collagen and a sugar was confirmed. A collagen solution was prepared so that the final concentration was 3% [w/v] or 0.4% [w/v]. Methods for the preparation were as follows: collagen solutions having final concentrations of 3% [w/v] and 0.4% [w/v] were produced by the same methods as those of Reference Example 3(1) and Reference Example 3(2), respectively. The kinds of the used sugars were glucose, sucrose, raffinose, and stachyose (the same as in those of Reference Examples 2 and 3), and the final concentration was 0.05 M. Each of the prepared solutions was measured for its time-dependent change in absorbance at 400 nm with a spectrophotometer while being heated at 37° C.

Figure 13:
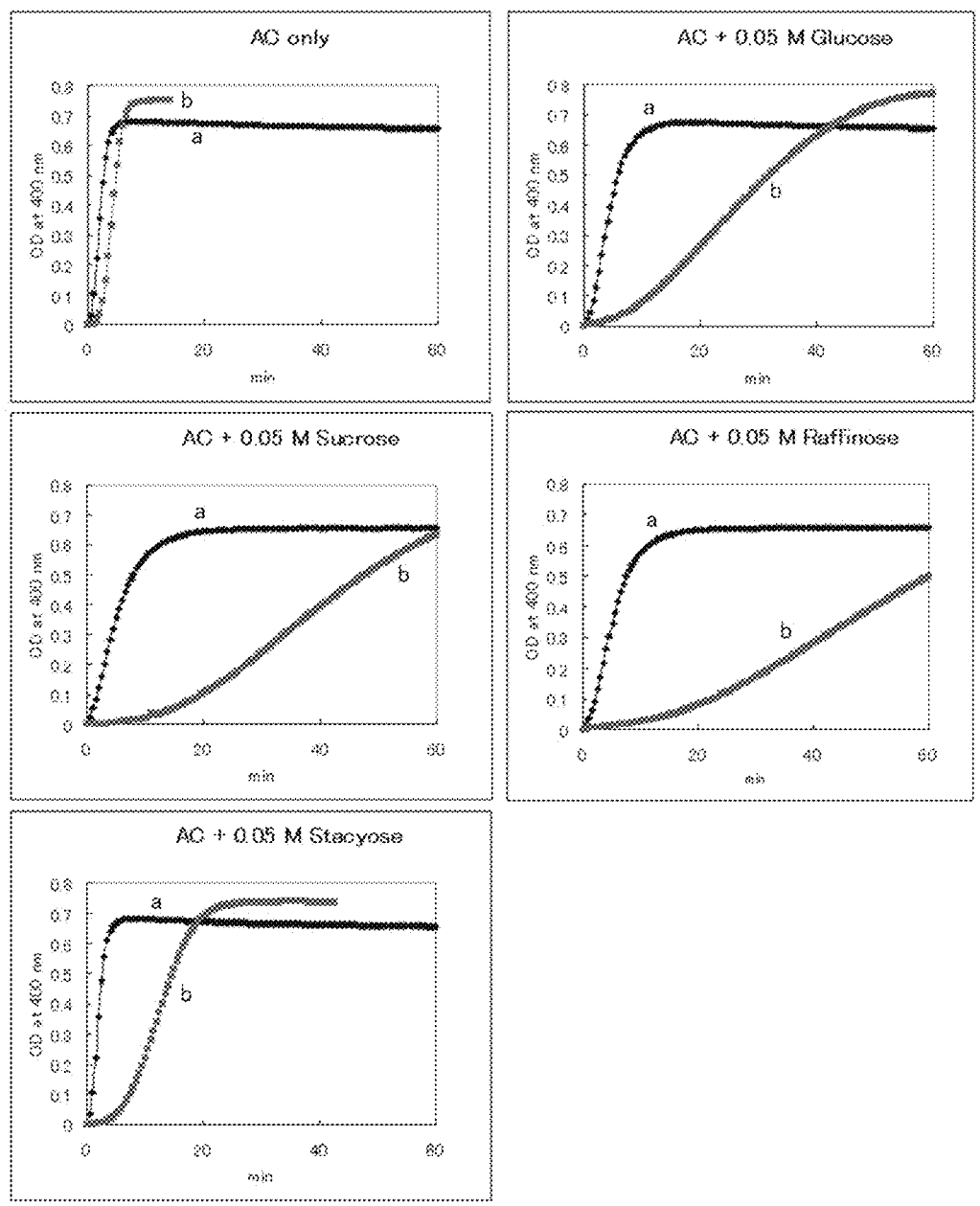
[FIG. 13] Graphs showing the results of confirmation of influences of addition of a sugar on gelation of a collagen at various concentrations in vitro. In the figures, "a" shows the result of a formulation containing a collagen at 3% [w/v], and "b" shows the result of a formulation containing a collagen at 0.4% [w/v] (Reference Example 5).

FIG. 13 show the results. In the figures, "a" shows the result of a formulation containing a collagen at 3% [w/v], and "b" shows the result of a formulation containing a collagen at 0.4% [w/v]. The results revealed that, in the case of adding an equal concentration of the sugar, as the concentration of the collagen became lower, the suppressing effect of the sugar became larger.

Reference Example 6

Spectroscopic Evaluation of Influences of Various Sugars on Gelation Ability of Collagen Solution Sugars including a monosaccharide to a pentasaccharide constructed only of glucose were used as sugars to be added, and the ability of each of the sugars to suppress the gelation of a collagen solution was confirmed by measuring a fibrillogenesis time.

The collagen solution was prepared so that the final concentration was 2% [w/v]. KOKEN ATELOCOLLAGEN IMPLANT [KOKEN CO., LTD.] was used as the collagen. The used sugars were glucose [Tokyo Chemical Industry Co., Ltd.], maltose [Wako Pure Chemical Industries, Ltd.], maltotriose [Wako Pure Chemical Industries, Ltd.], maltotetraose [Tokyo Chemical Industry Co., Ltd.], and maltopentaose [Wako Pure Chemical Industries, Ltd.]. The various sugars were dissolved in physiological saline [Otsuka Pharmaceutical Co., Ltd.] to prepare 1.25 M sugar solutions.

The collagen (final concentration: 2% [w/v]) and the various sugars (final concentration: 0.3 M) were filled into syringes, which were connected in series via a connector, followed by thorough mixing by reciprocation 50 times on ice. The contents were transferred to a 1.5-mL sampling tube, subjected to centrifugal defoaming (13,000 rpm, 4° C.), and then heated in a thermostat bath (37° C.). The state of the gelation was observed after 0 minutes, 10 minutes, 30 minutes, 60 minutes, 12 hours, 24 hours, and 3 days.

Figures 14, 15:
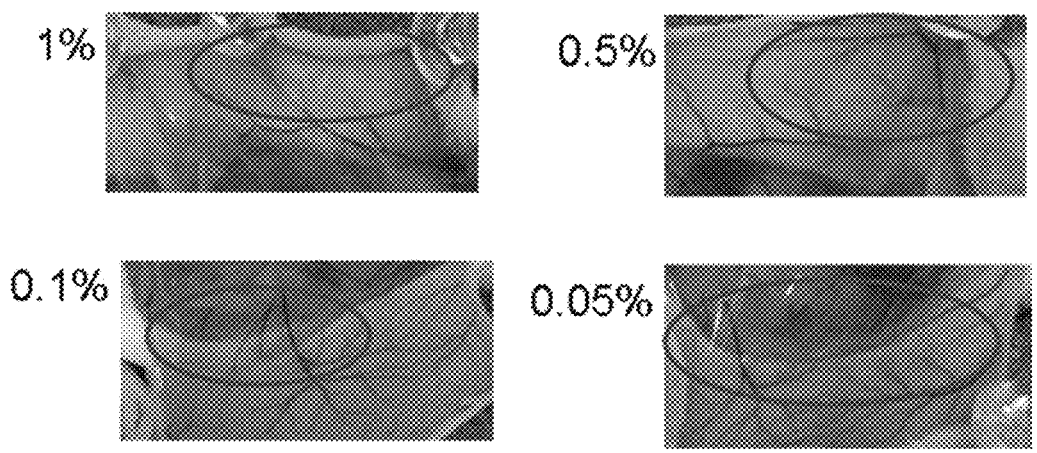
[FIG. 14] A table showing the results of confirmation of influences of addition of various sugars on gelation of a collagen in vitro (Reference Example 6).
[FIG. 15] Photographs showing the results of confirmation of influences of addition of a sugar on gelation of a collagen at various concentrations in vivo. In the figures, the numerical value described on the left of each photograph represents a concentration of a collagen in a formulation (Example 8).

FIG. 14 shows the results. Each of the monosaccharide, the disaccharide, and the trisaccharide had a large gelation suppressing effect, and the effect became the maximum in the disaccharide or the trisaccharide. In the case of the tetra- or more saccharide, it was confirmed that, as the number of sugar chains became larger, the gelation suppressing effect became lower. A possible mechanism through which the gelation suppressing effect becomes lower is that a physical or charge factor reduces the effect.

Example 8

Confirmation of Influences of Collagen Solutions Having Various Concentrations on In Vivo Gelation The following three kinds of ingredients were formulated: sucrose (final concentration: 0.25M) [Wako Pure Chemical Industries, Ltd.]; lysozyme (final concentration: 10 mg/mL) [Tokyo Chemical Industry Co., Ltd.]; and atelocollagen (final concentration: 0.05, 0.1, 0.5, or 1% [w/v]) (KOKEN ATELOCOLLAGEN IMPLANT [KOKEN CO., LTD.]). In the same manner as the technique of Example 2c), the formulation was performed by mixing sucrose with an atelocollagen solution and then adding lysozyme. 1 mL of each of formulations containing a collagen at 0.05% [w/v] and 0.1% [w/v] and 50 µL of each of formulations containing a collagen at 0.5% [w/v] and 1% [w/v] were administered to one site of the dorsal subcutis of mice (ICR, female, 8-week-old), and the state of the collagen solution was observed 24 hours after the administration.

FIG. 15 show the results. In the figures, the numerical value described on the left of each photograph represents the concentration of the collagen in the formulation. Gelation was confirmed in the formulations containing the collagen at 0.1% [w/v] and 0.05% [w/v] and the formulations containing the collagen at 0.5% [w/v] and 1% [w/v]. It was able to be confirmed that the formulations containing the collagen at concentrations of 0.05 to 1% [w/v] (containing 0.25 M sucrose and 10 mg/mL lysozyme) were capable of undergoing gelation 24 hours after the subcutaneous implantation in the mice.

Example 9

Confirmation of Influences of Various Sugars on In Vivo Gelation of Collagen Solution In the formulation of the present invention, the state of the gelation in the subcutis of the mice after 24 hours in the case of changing the kind of a sugar to be mixed was observed.

The kinds and concentrations of the sugars are as shown in Table 3 below.

TABLE 3

Kinds and final concentrations of used sugars

Figure 16:
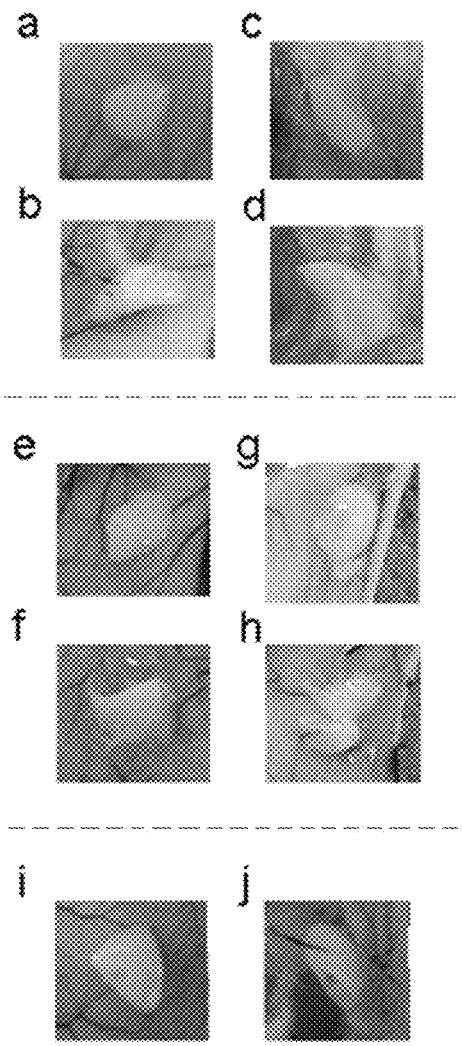
[FIG. 16] Photographs showing the results of confirmation of influences of changes in kind of a sugar on gelation of a collagen in vivo.

| Study group | Reference numeral in FIGS. 16 | Kind and final concentration of sugar |
|---|---|---|
| Comparison among kinds of sugars | a | 0.05M Glucose |
|  | b | 0.05M Sucrose |
|  | c | 0.05M Raffinose |
|  | d | 0.05M Stachyose |
| Comparison among monosaccharides | e | 0.5M Glucose |
|  | f | 0.25M Glucose |
|  | g | 0.5M Fructose |
|  | h | 0.25M Fructose |
| Comparison between disaccharides | i | 0.25M Sucrose |
|  | j | 0.25M Maltose |

The following three kinds of ingredients were formulated: any of the various sugars shown in Table 3; lysozyme (final concentration: 10 mg/mL); and atelocollagen (final concentration: 3% [w/v]) (KOKEN ATELOCOLLAGEN IMPLANT [KOKEN CO., LTD.]). In the same manner as the technique of Example 2c), the formulation was performed by dissolving sucrose in a physiological saline solution, mixing the solution with an atelocollagen solution, and adding lysozyme dissolved in a physiological saline solution. 50 µL of each of the formulations containing the sugars shown in Table 3 were administered to one site of the dorsal subcutis of mice (ICR, female, 9-week-old), and the state of the collagen solution 24 hours after the administration was observed.

FIG. 16 show the results. FIGS. 16a to 16j show the results of the formulations produced by using the kinds and sugar concentrations of sugars corresponding to the reference numerals in Table 3 above, respectively. Irrespective of the kinds and concentrations of the sugars, gelation was able to be confirmed in each of the formulations.

Example 10

Confirmation of Influences of Collagen Solutions Having Various Concentrations on In Vivo Gelation In the formulation of the present invention, the state of gelation in the case of changing a collagen concentration and a mouse subcutaneous implantation time was observed.

The following three kinds of ingredients were formulated: sucrose (final concentration: 0.25M) [Wako Pure Chemical Industries, Ltd.]; lysozyme (final concentration: 10 mg/mL) [Tokyo Chemical Industry Co., Ltd.]; and atelocollagen (final concentration: 0.05, 0.1, 0.5, or 1% [w/v]) (KOKEN ATELOCOLLAGEN IMPLANT [KOKEN CO., LTD.]). In the same manner as the technique of Example 2c), the formulation was performed by mixing sucrose with an atelocollagen solution and then adding lysozyme. 100 µL of each of the formulations were administered to one site of the dorsal subcutis of mice (ICR, female, 9-week-old), and the state of the collagen solution was observed 24 hours and 48 hours after the administration.

Figure 17:
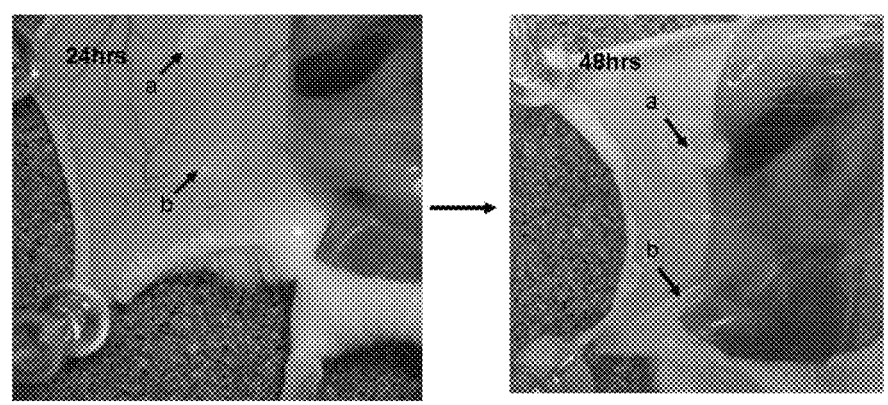
[FIG. 17] Photographs showing the results of confirmation of influences of addition of a sugar on gelation of a collagen at various concentrations in vivo. In the figures, "a" shows the result of a formulation containing a collagen at 1% [w/v], and "b" shows the result of a formulation containing a collagen at 0.5% [w/v] (Example 10).

At atelocollagen concentrations of 1% [w/v] (a) and 0.5% [w/v] (b), a gelated state was observed after 24 hours and 48 hours (FIG. 17). At 0.1% [w/v] and 0.05% [w/v], the collagen completely disappeared. No difference was found in the concentration and shape of the gelated collagen as well between the atelocollagen concentrations of 1% [w/v] and 0.5% [w/v] after 24 hours and 48 hours.

The formulation of the present invention contains sucrose at 0.25 M, and hence is expected to undergo gelation through the release of the sugar and the fibrillogenesis of atelocollagen after the absorption of the moisture of a body fluid based on an osmotic pressure. The sample having a concentration below a given one is predicted to have a low long-term retention property.

Reference Example 7

Spectroscopic Evaluation of Influences of Various Sugars on Gelation Ability of Collagen Solution The following sugars were used as sugars to be added, and an ability of the sugar to suppress the gelation of a collagen solution was confirmed by measuring a fibrillogenesis time.
Disaccharide: Sucrose
Monosaccharides: Glucose and Glucuronic Acid
Each of various sugar solutions was added to a collagen solution (pH 7.4, final concentration: 3% [w/v]) (KOKEN ATELOCOLLAGEN IMPLANT [KOKEN CO., LTD.]) so that the final concentration was 0.01 M, followed by mixing. The mixed solution was measured for its time-dependent change in absorbance at 400 nm with a spectrophotometer while being heated at 37° C.

Figure 18:
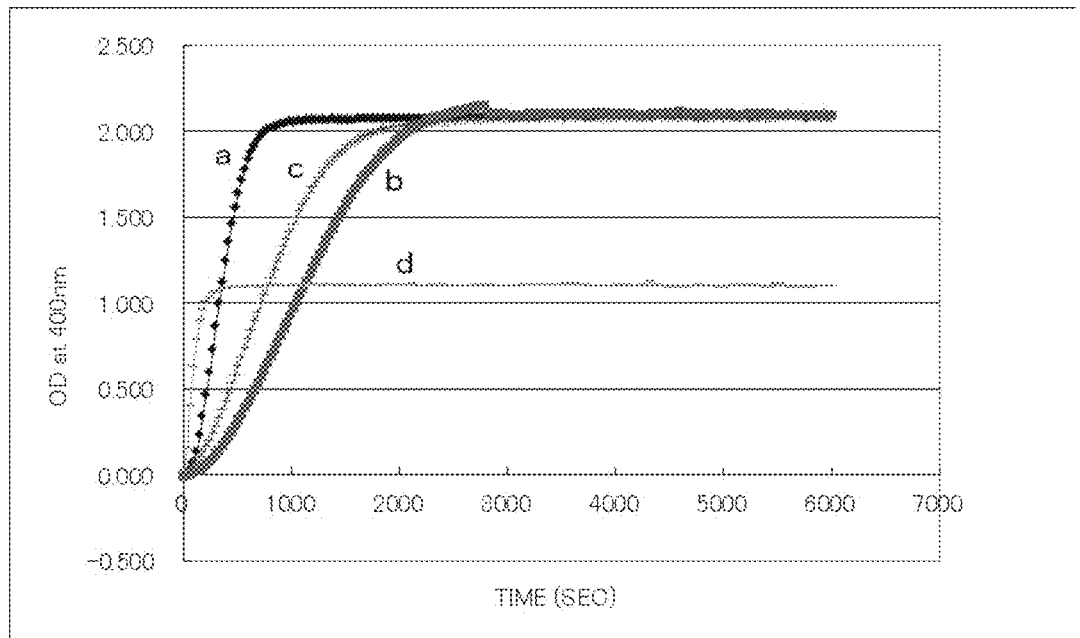
[FIG. 18] A graph showing the results of confirmation of addition of various sugars on gelation of a collagen in vitro. In the figure, "a" shows the result in the case of containing no sugar, "b" shows the result in the case of containing sucrose, "c" shows the result in the case of containing glucose, and "d" shows the result in the case of containing glucuronic acid (Reference Example 7).

FIG. 18 shows the results. In the figure, "a" shows the result of a formulation containing no sugar, "b" shows the result of a formulation containing sucrose, "c" shows the result of a formulation containing glucose, and "d" shows the result of a formulation containing glucuronic acid. Each of sucrose and glucose has a high gelation suppressing effect. Further, among the monosaccharides, glucuronic acid has a low gelation suppressing effect as compared to glucose.

Example 11

Confirmation of Drug Sustained-Release Ability in Formulation of Present Invention The formulation of the present invention containing a high molecular weight protein (thyroglobulin (669 kDa)) as a drug was produced, and its gelation 24 hours after subcutaneous implantation in mice was observed. The sustained-release amount of thyroglobulin was quantitatively measured by HPLC in a time-dependent manner.

The formulation of the present invention was produced by adjusting the final concentrations of atelocollagen, sucrose, and the protein to 3% [w/v], 0.25 M, and 10 mg, respectively. 3.5% [w/v] atelocollagen Lot. I-175, Kasai Lac, 2.5 M sucrose, and a 100-mg protein solution were mixed at a blending ratio of 8:1:1. First, syringes filled with atelocollagen and sucrose were connected in series on ice, followed by thorough mixing by reciprocation 50 times. The mixed liquid was mixed with the protein solution by syringe reciprocation 50 times immediately before subcutaneous injection into mice.

The mice were purchased from Japan SLC, Inc. ICR strain female mice were purchased at 7-week-old 1 week before use and used at 8-week old. The collagen mixed liquid was injected into three sites in an amount of 100 µL per site (n=3). Each of samples after 0, minutes, 30 minutes, 45 minutes, 1 hour, 3 hours, 6 hours, and 12 hours was extirpated and heated to 80° C. in an Eppendorf tube so as to denature the collagen into a solution form. Each of the samples was analyzed through use of Agilent HPLC and an SEC-4 gel filtration column to quantify the concentration of the protein in the gel. In the HPLC, thyroglobulin is eluted at 5.927 minutes.

Figure 19:
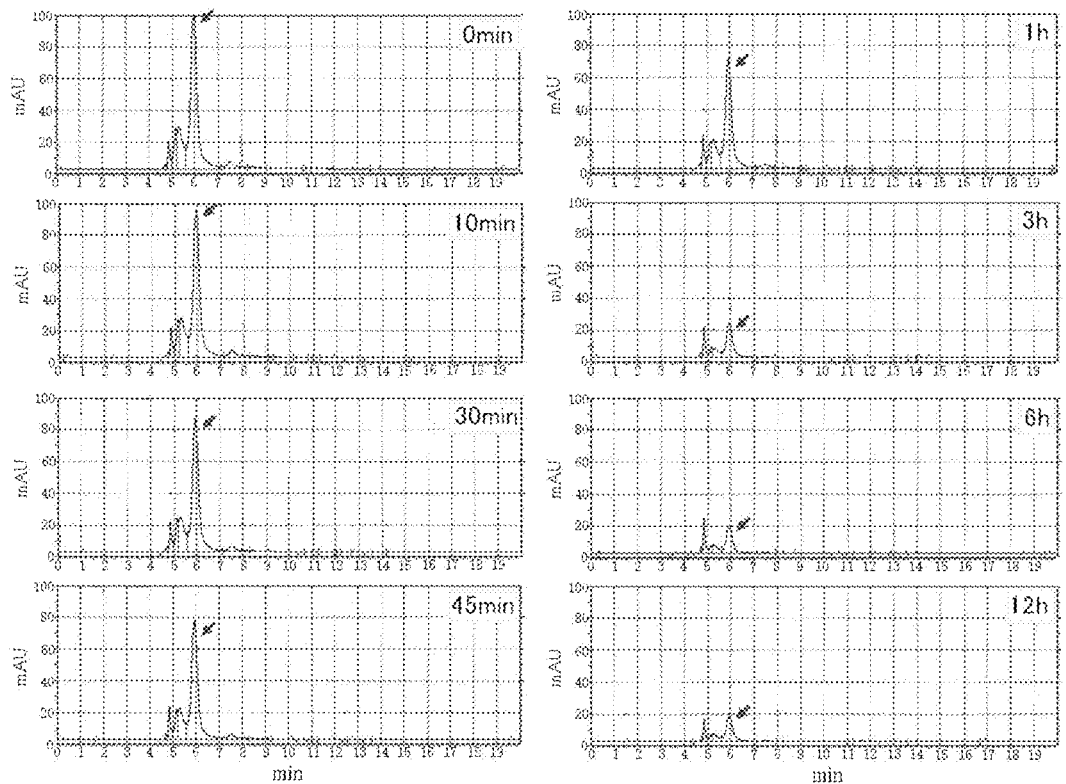
[FIG. 19] Charts showing the results of confirmation of an in vivo drug sustained-release ability of a sustained-release pharmaceutical composition containing thyroglobulin as a drug (Example 11).
Figure 20:
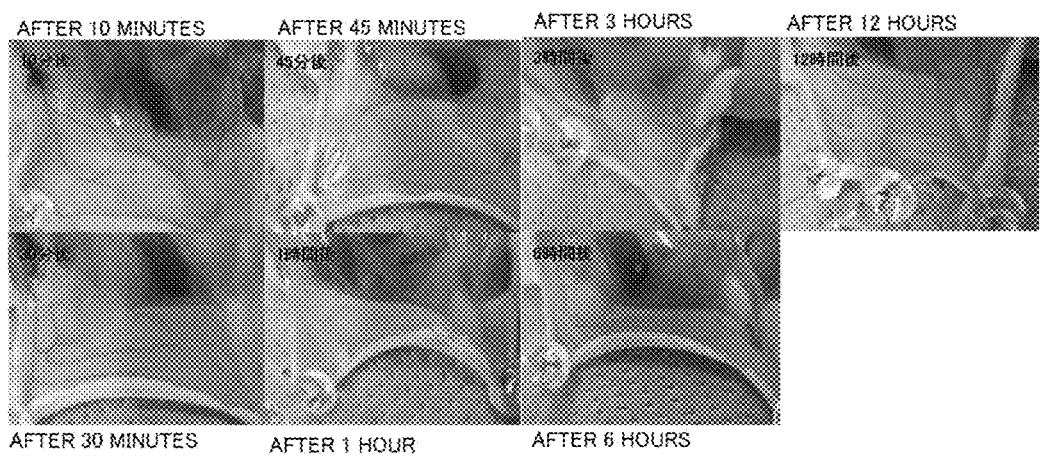
[FIG. 20] Photographs showing the results of confirmation of in vivo gelation of a sustained-release pharmaceutical composition containing thyroglobulin as a drug (Example 11).
Figure 21:
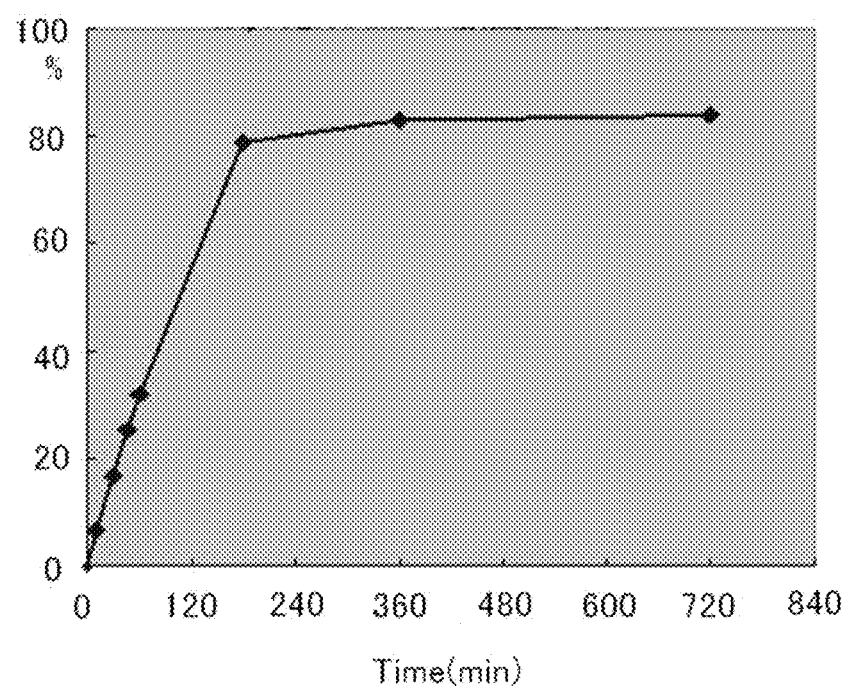
[FIG. 21] A graph showing the results of confirmation of a time-dependent change in in vivo drug release amount of a sustained-release pharmaceutical composition containing thyroglobulin as a drug (Example 11).

FIGS. 19 to 21 show the results. Until 3 hours after the injection, fast release was observed. After that, the rate was turned into a low sustained-release rate. This phenomenon was considered to have a close relationship with in vivo gelation. Irrespective of the molecular weight of a protein to be mixed, the release rate of the protein exhibited biphasic property of fast release in the initial period and slow release after gelation. A high release rate in the initial period and a time that elapses before gelation may be changed by changing the concentration of sucrose to be mixed.

INDUSTRIAL APPLICABILITY

According to the sustained-release pharmaceutical composition of the present invention, the drug as an active ingredient can be released in a sustained manner in an embodiment mode using immediately effective release and slow sustained release in combination in vivo, and the drug release rate can be controlled. Thus, the composition is useful. According to the present invention, the drug release rate can be controlled. Hence, there is a possibility that the treatment or the like of even an indication on which no effectiveness has been found hitherto can be performed.

Further, in general, in the preparation of a pharmaceutical composition having added thereto a collagen, it is necessary to manage a temperature so as to prevent the gelation of the collagen. According to the sustained-release pharmaceutical composition of the present invention, when a sugar is added to the collagen, its gelation is inhibited, and the composition can be prepared at room temperature, which can facilitate operations. Further, a drug, which has not been applicable to a preparation operation at low temperature, can be used. Thus, the composition is useful.

The invention claimed is:

1. A sustained-release pharmaceutical composition, comprising:
    a drug;
    a collagen, wherein the collagen is isolated atelocollagen; and
    at least one kind of sugar selected from a group consisting of a monosaccharide, a disaccharide, a trisaccharide, and a tetrasaccharide, which inhibits gelation of collagen, wherein the sustained-release pharmaceutical composition has a pH of from 4.0 to 10.0, and wherein the sustained-release pharmaceutical composition is in a liquid form before administration to a body, and has a property of undergoing gelation after the administration.

2. A sustained-release pharmaceutical composition according to claim 1, wherein the sugar has a concentration in the composition that is 0.01 M to 3 M.

3. A sustained-release pharmaceutical composition according to claim 1, wherein the sugar comprises at least one kind of sugar selected from disaccharides and trisaccharides.

4. A sustained-release pharmaceutical composition according to claim 1, wherein a concentration of the collagen is 0.01 to 30% by weight, and a concentration of the sugar is 0.01 M to 3 M.

5. A sustained-release pharmaceutical composition according to claim 1, wherein the sustained-release pharmaceutical composition controls a release rate of the drug.

6. A sustained-release pharmaceutical composition according to claim 1, wherein the drug comprises a protein.

7. A sustained-release pharmaceutical composition according to claim 1, wherein the sustained-release pharmaceutical composition comprises an angiogenesis regulator.

8. A sustained-release pharmaceutical composition according to claim 1, wherein the drug comprises basic fibroblast growth factor (bFGF).

9. A method of manufacturing the sustained-release pharmaceutical composition of claim 1, the method comprising mixing:
    a drug;
    isolated atelocollagen; and
    at least one king of sugar selected from monosaccharides, disaccharides, trisaccharides, and tetrasaccharides.

10. A sustained-release base, comprising:
    a collagen, wherein the collagen is isolated atelocollagen; and
    at least one kind of sugar selected from a group consisting of a monosaccharide, a disaccharide, a trisaccharide, and a tetrasaccharide, which inhibits gelation of collagen, wherein the sustained-release base is in a form of a liquid formulation, wherein the sustained-release base has a pH of from 4.0 to 10.0, and wherein a sustained-release pharmaceutical composition, which comprises the sustained-release base and a drug, is in a liquid form before administration to a body and has a property of undergoing gelation after the administration.

11. A method of controlling a drug release rate from the sustained-release pharmaceutical composition, the method comprising blending isolated atelocollagen with at least one kind of sugar selected from monosaccharides, disaccharides, trisaccharides, and tetrasaccharides.

* * * * *